(12) United States Patent
Suzuki et al.

(10) Patent No.: US 8,498,375 B2
(45) Date of Patent: Jul. 30, 2013

(54) X-RAY IMAGING APPARATUS

(75) Inventors: Masakazu Suzuki, Kyoto (JP); Hideki Yoshikawa, Kyoto (JP); Makoto Honjo, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 307 days.

(21) Appl. No.: 13/046,450

(22) Filed: Mar. 11, 2011

(65) Prior Publication Data

US 2011/0222646 A1    Sep. 15, 2011

(30) Foreign Application Priority Data

Mar. 12, 2010   (JP) .................................. 2010-055856

(51) Int. Cl.
*A61B 6/14* (2006.01)

(52) U.S. Cl.
USPC ............................................. 378/39; 378/62

(58) Field of Classification Search
USPC ............. 378/4–20, 38–40, 62, 101, 108–112
See application file for complete search history.

(56) References Cited

U.S. PATENT DOCUMENTS

| 7,249,886 B1 | 7/2007 | Chao et al. |
| 2008/0123816 A1 | 5/2008 | Mori et al. |

FOREIGN PATENT DOCUMENTS

| DE | 10 2008 025 201 A | 12/2009 |
| JP | S57-200132 A | 12/1982 |
| JP | H09-122118 A | 5/1997 |
| JP | 2001-54515 A | 2/2001 |
| JP | 2006-149493 A | 6/2006 |
| WO | WO 2009/063974 A | 5/2009 |
| WO | WO 2009/141766 A | 11/2009 |

*Primary Examiner* — Courtney Thomas
(74) *Attorney, Agent, or Firm* — DLA Piper LLP (US)

(57) ABSTRACT

An X-ray imaging apparatus includes an X-ray generation part, an X-ray detection part, and a revolution drive mechanism. The X-ray generation part has an X-ray generator including a cathode and an anode, and emits an X-ray beam from the X-ray generator. The X-ray detection part detects the X-ray beam. The revolution drive mechanism performs X-ray imaging by revolving the X-ray generation part and the X-ray detection part around the object while the X-ray generation part and the X-ray detection part are opposed to each other with said object interposed therebetween. The X-ray imaging apparatus controls a restriction part to thereby restrict an X-ray transmission in such a manner that the focal spot size of an X-ray beam used in X-ray CT imaging of a relatively narrow imaging region is smaller than the focal spot size of an X-ray beam used in X-ray CT imaging of a relatively large imaging region.

13 Claims, 22 Drawing Sheets

F I G. 2 A
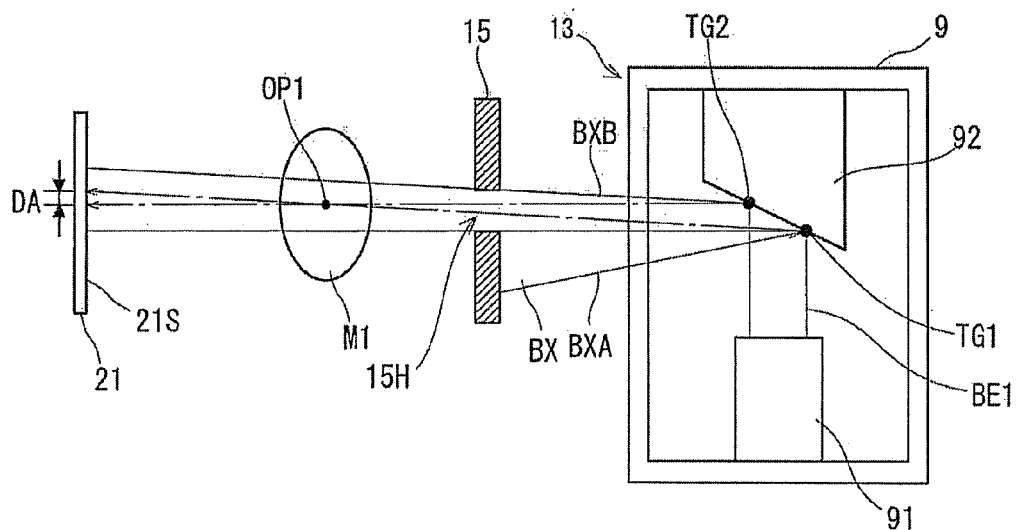
F I G. 2 B
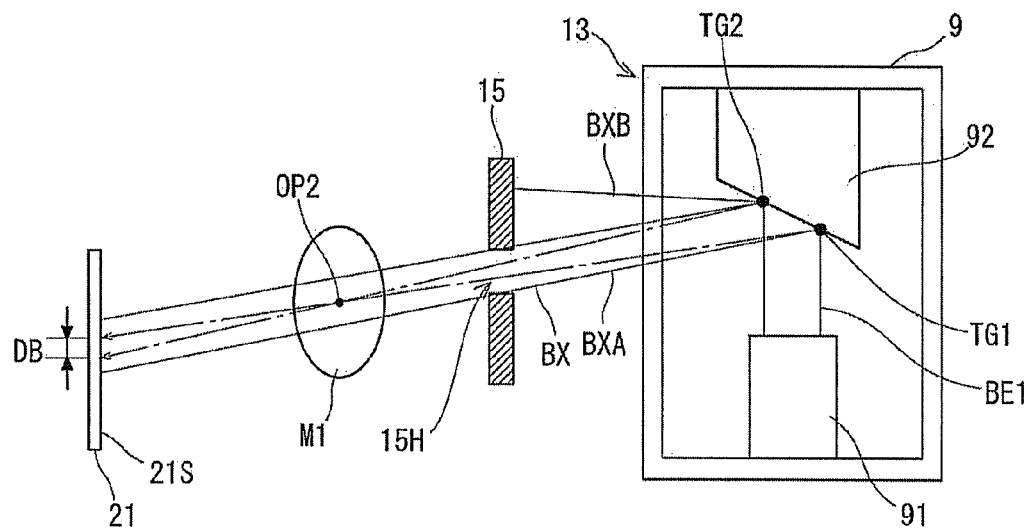

F I G. 9
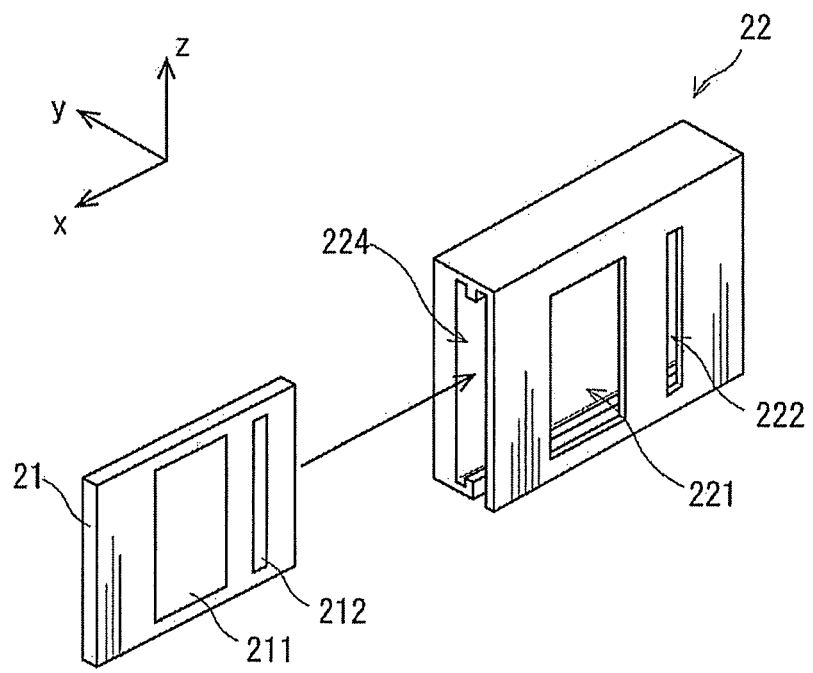

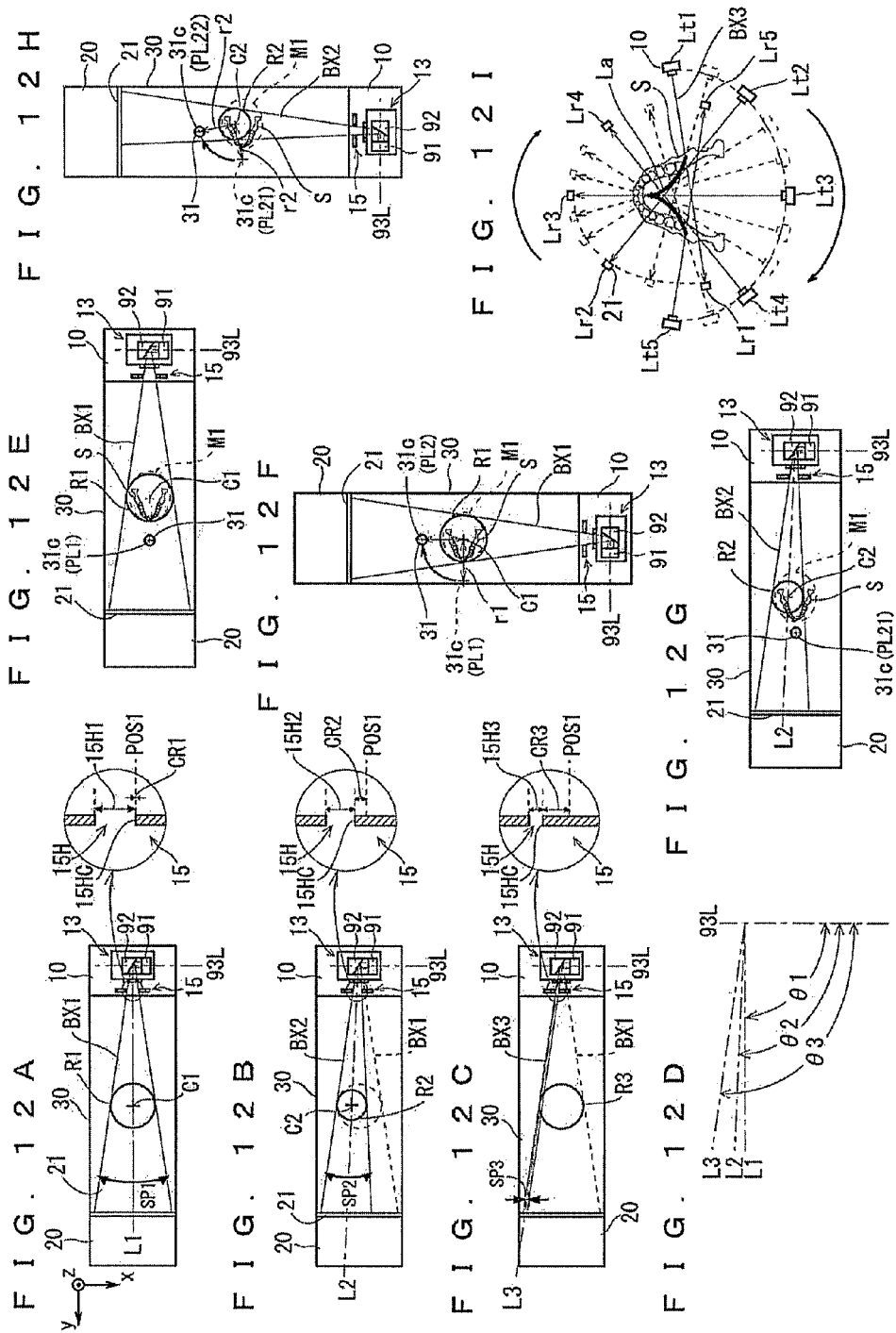

F I G . 1 3
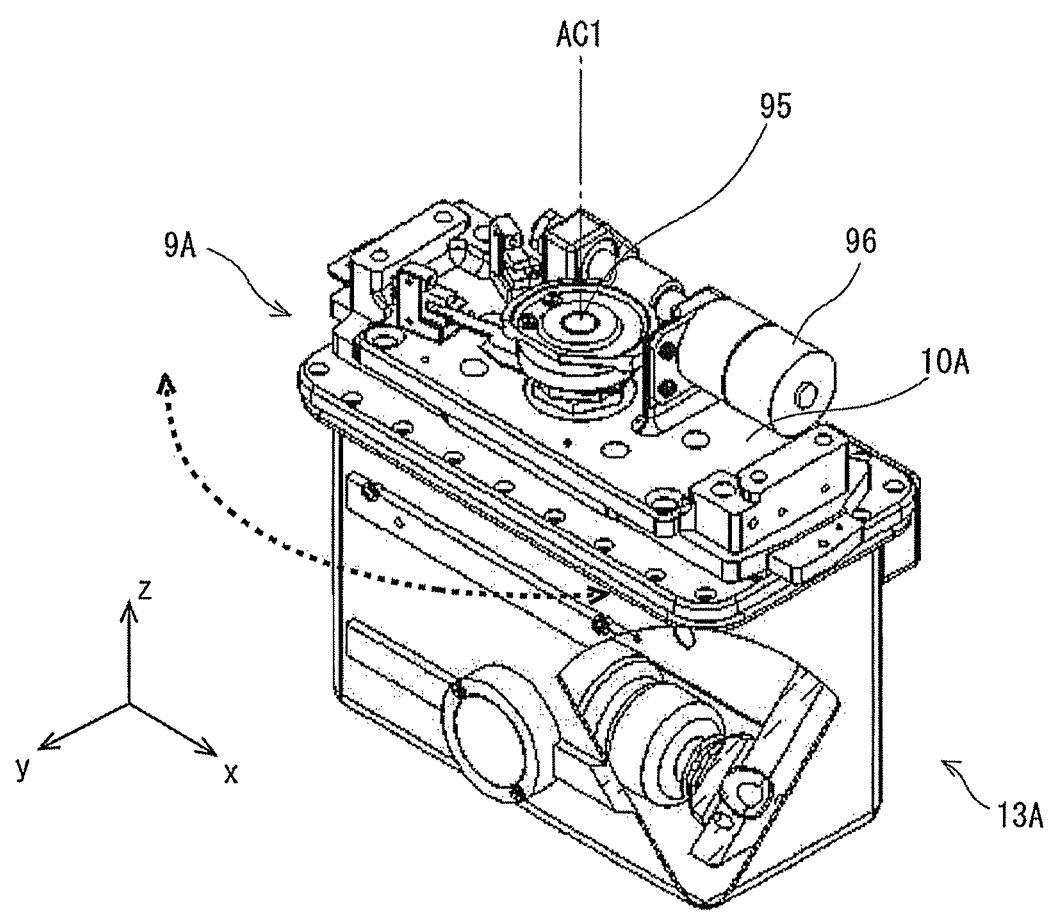

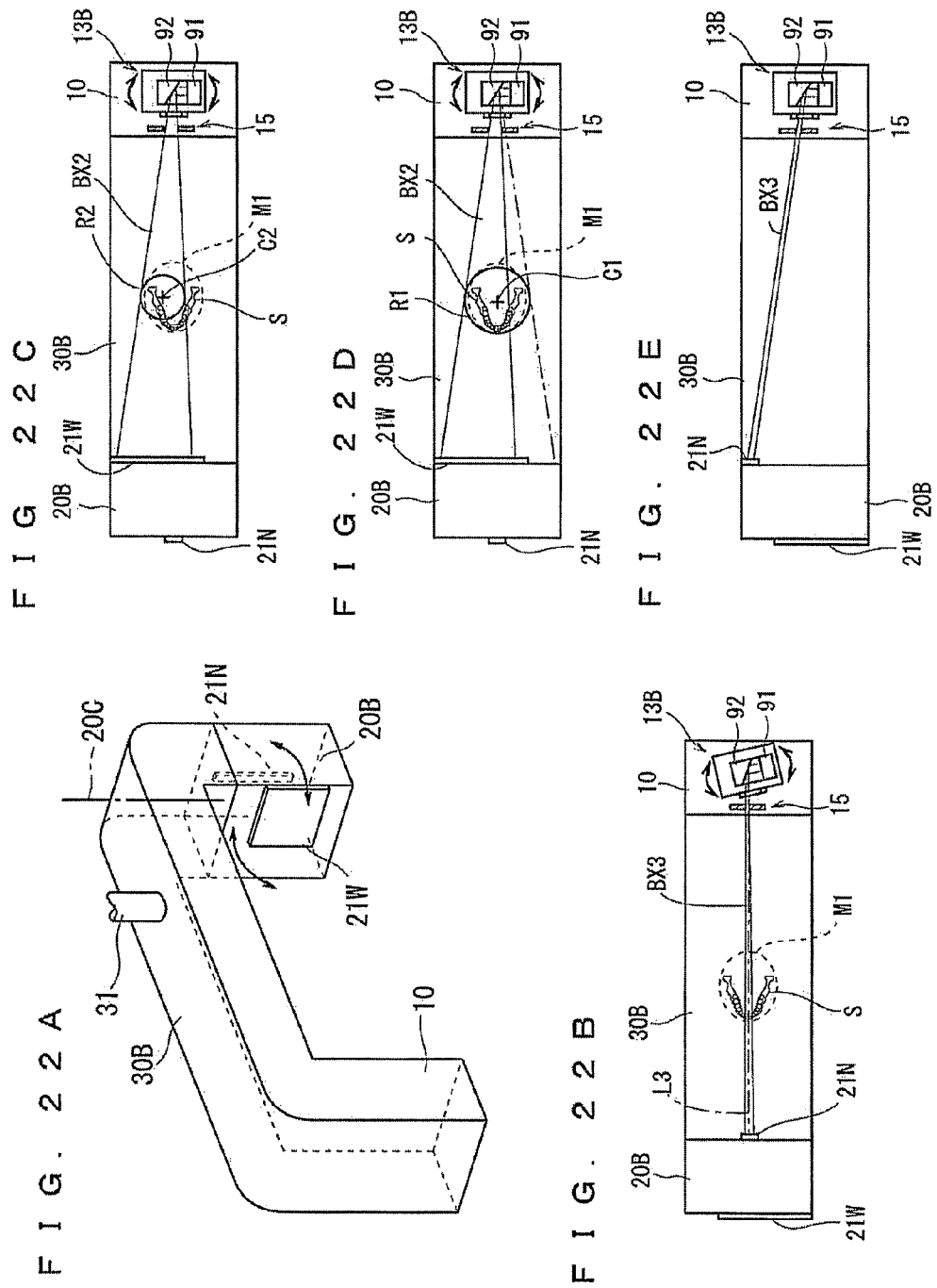

X-RAY IMAGING APPARATUS

BACKGROUND OF THE INVENTION

1. Field of the Invention

The present invention relates to a technique for X-ray CT imaging using an X-ray, and particularly to a technique of improving the resolution of a CT image.

2. Description of the Background Art

In the medical field, an X-ray imaging apparatus allowing various imaging modes to be performed by itself alone is used. For example, in the dental field, Japanese Patent Application Laid-Open No. 9-122118 (1997) discloses a multi-purpose type X-ray imaging apparatus which provides both a panoramic imaging mode and a CT imaging mode. In the panoramic imaging mode, a curved dental arch is imaged as an image developed in a plane. In the CT imaging mode, a tomographic image of a region of interest in a living organ is acquired.

In the X-ray imaging apparatus disclosed in Japanese Patent Application Laid-Open No. 9-122118 (1997), an X-ray source and an X-ray image detection means are revolved while being opposed to each other with an object interposed therebetween, and a plane including the orbit of the revolution of the X-ray source and X-ray image detection means is defined as a plane of revolution. A fan-shaped X-ray beam is radiated while selectively switching an opening portion (slit) provided at the front of the X-ray generator between a slit for cross-sectional tomographic imaging (CT) and a slit for curved-plane tomographic imaging (panorama). The slit for cross-sectional tomographic imaging is elongated in a direction parallel to the plane of revolution, and the slit for curved-plane tomographic imaging is elongated in a direction perpendicular to the plane of revolution of a revolving arm.

Japanese Patent Application Laid-Open No. 9-122118 (1997) also discloses rotating the whole of the X-ray generator and the whole of an X-ray imager around an emission central axis connecting the X-ray generation part to the X-ray detection part, to selectively switch the arrangement of the X-ray generator and the X-ray imager between an arrangement for cross-sectional tomographic imaging and an arrangement for the panoramic imaging.

Additionally, several techniques have been proposed for improving the resolution of an image by improving a method of forming an X-ray beam (for example, Japanese Patent Application Laid-Open No. 2001-54515, Japanese Patent Application Laid-Open No. 2006-149493, and Japanese Patent Application Laid-Open No. 57-200132 (1982)).

More specifically, Japanese Patent Application Laid-Open No. 2001-54515 discloses CT imaging using a cone-beam X-ray in which a part of a cone-beam X-ray having a large effective focal spot is blocked by a leaf made of an X-ray blocking material.

Japanese Patent Application Laid-Open No. 2006-149493 discloses X-ray breast imaging in which an X-ray is partially blocked by a displaceable blocking plate so that X-ray emission can be performed using a part of the X-ray having a certain degree or more of intension and having as small a focal spot size as possible.

Japanese Patent Application Laid-Open No. 57-200132 (1982) discloses CT imaging in which an X-ray is generated at a plurality of different spots on a target surface of an X-ray tube at the anode side.

While, several techniques have been proposed for improving the resolution by reducing a focal spot size, a technique for improving an image resolving power in a multi-purpose type X-ray imaging apparatus which allows various types of X-ray imaging having different X-ray radiation ranges is not yet known.

Particularly, in the field of an X-ray imaging apparatus for dental use, there has been a demand that an X-ray beam having the optimum focal spot size for each of different modes be set in a multi-purpose type X-ray imaging apparatus allowing an imaging mode to be switched between a panoramic imaging mode, an X-ray CT imaging mode, and the like.

The present invention is made in view of the problem described above, and an object of the present invention is to provide a technique of improving the resolution of an X-ray image in an X-ray imaging apparatus which allows various types of X-ray imaging having different X-ray radiation ranges.

In the above-described multi-purpose type X-ray imaging apparatus, and particularly in the X-ray imaging apparatus for dental use, for example, in the panoramic imaging mode, a so-called narrow-type X-ray beam is used in which the spread of an X-ray beam radiated to an object for imaging is much smaller when compared with an X-ray CT imaging mode. In the X-ray CT imaging, on the other hand, it is necessary to use an X-ray beam whose spread in a horizontal direction corresponds to the size of an imaging area, in order to cover the imaging area.

In the panoramic imaging, a better image quality is obtained by making a focal spot size in the horizontal direction smaller. However, in a conventional apparatus, an X-ray is blocked from both sides thereof in order to adjust the spread of a radiated X-ray beam in accordance with switching between the X-ray CT imaging mode and the panoramic imaging mode. In a case where an X-ray radiation range is narrowed in this manner, the apparent size of a focal spot is hardly changed. Therefore, it has been difficult to improve the image quality by, for example, increasing the sharpness of an X-ray image or reducing blurring (so-called defocusing or reflection blurring), because when imaging is performed using a narrowly-spread X-ray beam, an X-ray passing through a certain spot on an X-ray emission path is largely dispersed on an X-ray detection surface so that the resolution is lowered.

In a case of an X-ray imaging apparatus providing only X-ray imaging using an X-ray beam narrowly spread in the horizontal direction, such as the panoramic imaging, the imaging may be performed using an X-ray beam having a small focal spot size. However, a certain degree of focal spot size is required in order to ensure an emission region for the CT imaging mode using an X-ray beam largely spread in the horizontal direction. Accordingly, in an X-ray imaging apparatus providing both of X-ray imaging using an X-ray beam widely spread in the horizontal direction and X-ray imaging using an X-ray beam narrowly spread in the horizontal direction, an X-ray imaging apparatus has been demanded which can meet the requirement that the sharpness of an X-ray image be further increased in X-ray imaging using an X-ray beam narrowly spread in the horizontal direction.

Particularly, in a case when a cone-beam is used for the CT imaging, the panoramic imaging can be also performed using a narrow X-ray beam obtained by restricting the spread of the cone-beam in the horizontal direction. Here, an X-ray imaging apparatus which can increase the sharpness of an X-ray image obtained by panoramic imaging also has been in demand.

As for the CT imaging mode, too, in a CT imaging apparatus providing both of a large or wide Field of View (FOV) imaging mode which is a CT imaging mode using an X-ray beam widely spread in the horizontal direction and a small or narrow FOV imaging mode which is a CT imaging mode using an X-ray beam narrowly spread in the horizontal direction, an X-ray imaging apparatus has been demanded which responds to a problem that the sharpness of an X-ray image should be increased in the small FOV imaging mode.

Moreover, an X-ray imaging apparatus has been demanded which can, in addition to increasing the sharpness of the X-ray image in each imaging mode, improve the image quality with an enhanced accuracy and a low cost, and moreover suppress the amount of X-ray exposure of an object.

In the X-ray CT imaging mode, the degree of spread of an X-ray beam used is sometimes different between a case where an imaging region is relatively large or wide and a case where an imaging region is relative small or narrow. In such a case, similarly to the above-described case, it is demanded to improve the image quality when imaging is performed by using a narrowly spread X-ray beam.

Japanese Patent Application Laid-Open No. 9-122118 (1997) gives no consideration to a focal spot size corresponding to each imaging type, and merely switches an X-ray radiation field between a radiation field elongated in a direction parallel to the plane of revolution and a radiation field elongated in the direction perpendicular to the plane of revolution in accordance with whether the imaging is a cross-sectional tomographic imaging or the panoramic imaging. Thus, it is difficult to optimally increase the sharpness of an X-ray image in accordance with the type of imaging.

In the X-ray imaging apparatus disclosed in Japanese Patent Application Laid-Open No. 2001-54515, only a single type of CT imaging mode is provided, and the mode itself cannot be switched.

In the X-ray imaging apparatus disclosed in Japanese Patent Application Laid-Open No. 2006-149493, an X-ray radiation range can be adjusted, but only a single type of X-ray imaging mode such as X-ray breast imaging is provided, and the mode itself cannot be switched.

The X-ray imaging apparatus disclosed in Japanese Patent Application Laid-Open No. 57-200132 (1982) does not aim at changing the focal spot size of an X-ray beam, but aims at obtaining an X-ray image of a plurality of slice planes by using X-rays from a plurality of focal points. It is impossible that the sharpness of an X-ray image is increased in an imaging mode using an X-ray beam spread more narrowly.

Any of the Patent Documents mentioned above does not contain the idea of making a control such that the angle formed between the central axis of an X-ray beam emitted from an X-ray generation part and a straight line connecting the cathode and the anode of an X-ray generation source is changed by switching an X-ray imaging mode in accordance with a reduction in an X-ray beam radiation range. Therefore, it is impossible that the sharpness of an X-ray image is increased in an imaging mode using an X-ray beam spread more narrowly. Additionally, it is impossible to adjust the focal spot size in accordance with a mode and to increase the sharpness of an X-ray image with a simple structure and a low cost. Furthermore, it is impossible to allow the CT imaging to be performed in imaging regions having different sizes and to adjust the focal spot size, that is, to increase the sharpness of an X-ray image, in accordance with the size of the imaging region.

SUMMARY OF THE INVENTION

In a first aspect, an X-ray imaging apparatus which performs X-ray imaging, includes: an X-ray generation part including a cathode and an anode, a surface of the anode opposed to the cathode being formed as an inclined surface inclined with respect to a straight line connecting the anode and the cathode to each other, the inclined surface being formed by an X-ray generation surface which receives an electron beam from the cathode and generates an X-ray, the X-ray generation part having an X-ray generation source for generating an X-ray beam which is a flux of the X-ray generated by the X-ray generation surface toward a direction of reflection from the electron beam, the X-ray beam generated by the X-ray generation source being radiated toward an object; an X-ray detection part which detects the X-ray beam emitted toward the object; a revolution drive mechanism which performs X-ray imaging by revolving the X-ray generation part and the X-ray detection part around the object while the X-ray generation part and the X-ray detection part are opposed to each other with the object interposed therebetween; an imaging mode selection section which selects an imaging mode from a plurality of imaging modes having different ranges of radiation of the X-ray beam radiated to the object for X-ray imaging; and an emission control section which controls the X-ray generation part in such a manner that an angle formed between the straight line connecting the cathode and the anode of the X-ray generation source and a central axis of the X-ray beam emitted from the X-ray generation part is increased in an imaging mode having a smaller or narrower range of radiation of the X-ray beam.

In the X-ray imaging apparatus according to the first aspect, a control can be made such that the angle formed between the straight line connecting the cathode and the anode of the X-ray generation source and the central axis of the X-ray beam emitted from the X-ray generation part is increased in the imaging mode having a smaller range of radiation of the X-ray beam. This can provide an excellent effect that an X-ray image having excellent resolution can be obtained in each mode.

In a second aspect, in the X-ray imaging apparatus according to the first aspect: a restriction section restricts the X-ray beam, the restriction section restricting a range of radiation of the X-ray beam by allowing a part of the X-ray beam to pass therethrough in an opening portion thereof; and in accordance with a selection signal outputted by the imaging mode selection section, the emission control section controls the restriction section so as to change the range of radiation of the X-ray beam used for the X-ray imaging, by increasing the amount of restriction of an emission range of the X-ray beam at a portion thereof close to the cathode in an imaging mode having a smaller or narrower range of radiation of the X-ray beam.

The X-ray imaging apparatus according to the second aspect can provide an excellent effect that the focal spot size can be changed easily and at a low cost.

In a third aspect, in the X-ray imaging apparatus according to the first aspect, the emission control section controls the displacement of the X-ray generation source in accordance with a selection signal outputted by the imaging mode selection section, in such a manner that the angle formed between the straight line connecting the cathode and the anode of the X-ray generation source and the central axis of the X-ray beam emitted from the X-ray generation part is increased in an imaging mode having a smaller/narrower range of radiation of the X-ray beam.

In the X-ray imaging apparatus according to the third aspect, since the focal spot size can be easily changed by displacing the X-ray generation source, the structure of the restriction part for restricting the range of radiation of the X-ray beam can be simplified.

In a fourth aspect, in the X-ray imaging apparatus according to the third aspect, the emission control section controls the displacement of the X-ray generation source by controlling an angle of rotation of the X-ray generation source relative to the X-ray generation part.

In the X-ray imaging apparatus according to the fourth aspect, the focal spot size can be easily changed by rotating the X-ray generation source, and additionally, in panoramic imaging for example, a narrow beam can be radiated toward a middle portion of the X-ray detector similarly to the conventional X-ray imaging apparatus. Therefore, the movement of the X-ray generation part and the X-ray detection part can be controlled on the same orbit as in the conventional X-ray imaging apparatus. Moreover, the central axis of the X-ray beam can be made incident on a detection surface of the X-ray detector of the X-ray detection part in a direction perpendicular thereto. This can reduce image distortion, too.

In a fifth aspect, in the X-ray imaging apparatus according to the fourth aspect, the X-ray generation source is rotated around a rotation shaft, to be rotated relative to the X-ray generation part.

In the X-ray imaging apparatus according to the fifth aspect, the same effects as those of the X-ray imaging apparatuses according to the third and fourth aspects can be obtained, and additionally an effect that the focal spot size can be changed easily and at a low cost can be obtained.

In a sixth aspect, in the X-ray imaging apparatus according to the fifth aspect: the revolution drive mechanism revolves the X-ray generation part and the X-ray detection part around a revolution shaft; and an axial direction of the rotation shaft of the X-ray generation source is set to be a direction parallel to an axial direction of the revolution shaft of the revolution drive mechanism.

In the X-ray imaging apparatus according to the sixth aspect, the same effects as those of the X-ray imaging apparatuses according to the third to fifth aspects can be obtained, and additionally an effect that the focal spot size can be changed with enhanced accuracy can be obtained.

In a seventh aspect, in the X-ray imaging apparatus according to any one of the third to sixth aspects: a restriction section restricts the X-ray beam, the restriction section restricting a range of radiation of the X-ray beam by allowing a part of the X-ray beam to pass therethrough in an opening portion thereof; and in accordance with the selection signal outputted by the imaging mode selection section, the emission control section reduces an opening width of the opening portion in the imaging mode having a smaller/narrower range of radiation of the X-ray beam.

In the X-ray imaging apparatus according to the seventh aspect, the same effects as those of the X-ray imaging apparatuses according to the third to sixth aspects can be obtained, and additionally an effect that only an X-ray necessary for a diagnosis can be radiated to the object easily and at a low cost.

In an eighth aspect, in the X-ray imaging apparatus according to any one of the first to seventh aspects, the plurality of imaging modes include an X-ray CT imaging mode for performing X-ray CT imaging and a panoramic imaging mode for performing panoramic imaging In the X-ray imaging apparatus according to the eighth aspect, a sharp X-ray image can be obtained, particularly even when a mode is switched to a panoramic imaging mode in an X-ray imaging apparatus which provides both CT imaging and panorama imaging.

In a ninth aspect, in the X-ray imaging apparatus according to any one of the first to seventh aspects, the plurality of imaging modes include a plurality of X-ray CT imaging modes for performing X-ray CT imaging having different sizes of X-ray imaging regions.

In the X-ray imaging apparatus according to the ninth aspect, in an X-ray imaging apparatus which allows CT imaging to be performed in both of a large/wide X-ray imaging region and a small/narrow X-ray imaging region, a sharp X-ray image can be obtained, particularly even when the mode is switched to a mode for performing CT imaging in a small X-ray imaging region.

In a tenth aspect, in the X-ray imaging apparatus according to the eighth or ninth aspect, the X-ray CT imaging mode further includes a large-radiation-field X-ray CT imaging mode for performing X-ray CT imaging in a large X-ray imaging region, and a small-radiation-field X-ray CT imaging mode for performing X-ray CT imaging in a small. X-ray imaging region.

In the X-ray imaging apparatus according to the tenth aspect, a sharp X-ray image can be obtained particularly when a mode is switched to a panoramic imaging mode in, for example, an X-ray imaging apparatus which provides both CT imaging and panorama imaging. Additionally, the CT imaging mode can be switched between a CT imaging mode for a relatively large X-ray imaging region and a CT imaging mode for a relatively small X-ray imaging region. Particularly, even when the mode is switched to a mode for performing CT imaging in a small X-ray imaging region, a sharp X-ray image can be obtained.

In an eleventh aspect, in the X-ray imaging apparatus according to any one of the eighth to tenth aspects, the X-ray CT imaging mode includes an offset-scanning X-ray CT imaging mode.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 2A and 2B are diagrams schematically showing the X-ray tube according to the first preferred embodiment;

FIG. 9 is a perspective view showing a detector holder;

FIGS. 12A, 12B, 12C, 12D, 12E, 12F, 12G, 12H, and 12I are schematic top views of the X-ray imaging apparatus, showing a situation where X-ray imaging according to the first preferred embodiment is performed;

FIG. 13 is a perspective view showing an X-ray generator according to a second preferred embodiment;

FIGS. 22A, 22B, 22C, 22D, and 22E are diagrams for explaining a revolving arm 30B according to a seventh preferred embodiment.

EMBODIMENT FOR CARRYING OUT THE INVENTION

Hereinafter, some preferred embodiments will be described in detail with reference to the accompanying drawings. Any configuration described in these preferred embodiments is merely illustrative, and should not be construed as limiting the scope of the present invention.

1. First Preferred Embodiment

1.1. Outline

Figure 1A:
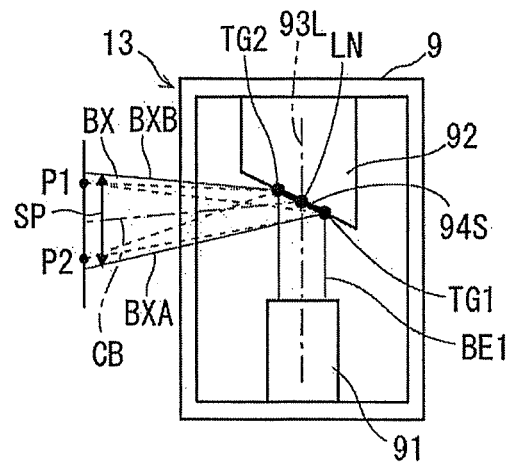
FIGS. 1A, 1B, and 1C are diagrams schematically showing an X-ray tube according to a first preferred embodiment.
Figure 1B:
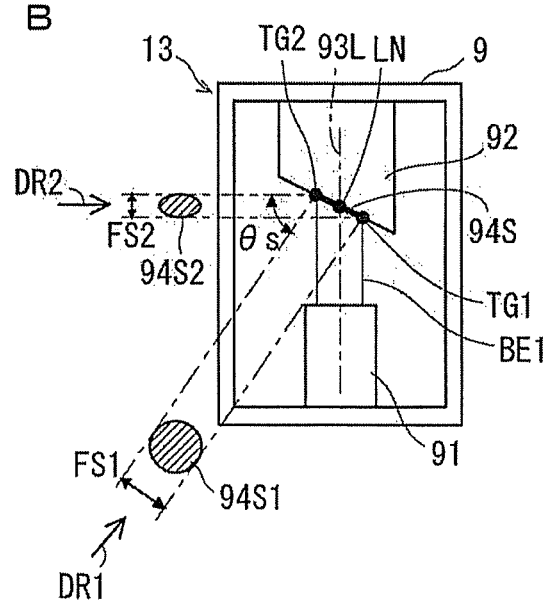
Figure 1C:
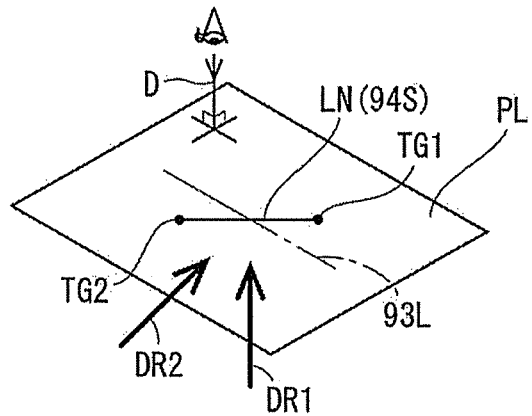

FIGS. 1A, 1B, 1C, 2A, and 2B are diagrams schematically showing an X-ray tube 9 according to a first preferred embodiment. FIGS. 1A, 1B, 2A, and 2B are diagrams schematically showing the X-ray tube 9 as viewed along a line-of-sight direction D which is a direction of seeing an inclined surface of a target surface 94S as shown in FIG. 1C.

As shown in FIG. 1A, in the X-ray tube 9 serving as an X-ray generation source, a cathode 91 including a filament and an anode 92 arranged at a distance from the cathode 91 are provided. A surface of the anode 92 opposed to the cathode 91 is formed as an inclined surface inclined at a predetermined angle relative to a straight line 93L (a straight line extending in parallel with a direction of emission of an electron beam) passing through the center of a longitudinal axis of each of the cathode 91 and the anode 92 and connecting the cathode 91 and the anode 92 to each other. A target surface 94S (a portion illustrated with the bold line) is provided on the inclined surface.

An electron beam BE1 emitted from the cathode 91 collides with the target surface 94S, and thereby an X-ray beam BX having a predetermined spread is emitted from the target surface 94S toward a reflection direction of reflection from a direction of travel of the electron beam BE1. That is, the target surface 94S forms an X-ray generation surface which generates an X-ray.

In a radiation range of the X-ray beam BX, positions P1 and P2 existing on a line parallel to the electron beam BE1 (the position P1 is farther from the cathode 91 than the position P2 is) are assumed. An apparent size of the target surface 94S when seen from the position P1 is smaller than an apparent size of the target surface 94S when seen from the position P2.

In the following, the description that an element X is larger than an element Y means the same as the description that the element Y is smaller than the element X; and also the description that an element X is smaller than an element Y means the same as the description that the element Y is larger than the element X.

In the target surface 94S serving as the X-ray generation surface, there are a point TG1 closest to the cathode 91 and a point TG2 farthest from the cathode 91. A line segment LN connecting the point TG1 and the point TG2 to each other is assumed. Both the straight line 93L and the line segment LN are located on a plane PL shown in FIG. 1C.

The X-ray beam BX shown in FIG. 1A has a radiation range (spread) SP as seen along the line-of-sight direction D. In an illustrated example, the target surface 94S is a plane, and the above-mentioned plane PL is a plane perpendicular to the target surface 94S. The line-of-sight direction D is a direction perpendicular to both the straight line 93L and the line segment LN. The line-of-sight direction D is a direction in which the distance between the point TG1 and the point TG2 appears the largest.

The distance between the point TG1 and the point TG2 when seen from the position P1 is smaller than the distance between the point TG1 and the point TG2 when seen from the position P2. That is, in the X-ray beam BX, at a position farther from the cathode 91 (that is, closer to the anode 92), a larger apparent size (focal spot size) of the X-ray generation surface is observed.

Here, a more specific description will be given of the focal spot size which is the apparent size of the target surface 94S serving as the X-ray generation surface.

When the target surface 94S shown in FIG. 1B is seen in a line-of-sight direction DR1, the target surface 94S appears as indicated by the reference sign 94S1. In the illustrated example, the line-of-sight direction DR1 is a direction perpendicular to the target surface 94S. The line-of-sight direction DR1 is a direction in which the target surface 94S appears the largest.

When the target surface 94S is seen in a line-of-sight direction DR2 which is inclined at an angle of θs from the line-of-sight direction DR1 toward the side opposite to the straight line 93L, the target surface 94S appears as indicated by the reference sign 94S2.

When the distance between the point TG1 and the point TG2 as seen along the line-of-sight direction DR1 is defined as FS1 and the distance between the point TG1 and the point TG2 as seen along the line-of-sight direction DR2 is defined as FS2, FS2 is smaller than FS1.

In this manner, the size of the target surface 94 serving as the X-ray generation surface varies depending on an angle of view and a line-of-sight direction.

Here, the size of the X-ray generation surface which varies depending on the angle of view and the line-of-sight direction is referred to as a "focal spot size". The focal spot size becomes smaller as the angle θs increases.

Spreads of an X-ray flux of the X-ray beam BX generated from the target surface 94 include the spread SP shown in FIG. 1A which is observed when seen along the line-of-sight direction D. In the illustrated example, the spread SP is a spread extending between an end portion BXA and an end portion BXB of the X-ray flux. The end portion BXA is closest to the cathode 91, and the end portion BXB is farthest from the cathode 91. The spread SP is a spread observed when seen along a direction perpendicular to both of the straight line 93L and the center CB of the X-ray flux.

The focal spot size changes depending on a position at which restriction is performed in a case where the above-described spread SP is partially restricted to restrict the radiation range.

As shown in FIGS. 2A and 2B, a part of the X-ray beam BX is restricted by a restriction part 15 being a restriction section 15 which restricts an X-ray radiation range, so that only an X-ray passing through an opening 15H being an opening portion 15H is allowed to pass. In FIGS. 2A and 2B, the same opening width of the X-ray pass-through opening 15H is adopted. However, in FIG. 2A, the opening 15H is located at a position closer to the end portion BXB, while in FIGS. 2B, the opening 15H is located at a position closer to the end portion BXA.

In FIG. 2A, it is assumed that the X-ray passing through the opening 15H is transmitted through a point OP1 within an object M1. In FIGS. 2B, it is assumed that the X-ray passing through the opening 15H is transmitted through a point OP2 within the object M1.

The X-ray generated from the point TG1 and the X-ray generated from the point TG2 are transmitted through the point OP1 of FIG. 2A, to form an image on an X-ray detection surface 21S of an X-ray detector 21. The X-ray generated from the point TG1 and the X-ray generated from the point TG2 are transmitted through the point OP2 of FIGS. 2B, to form an image on the X-ray detection surface 21S of the X-ray detector 21.

A distance DA between an imaging point of the X-ray generated from the point TG1 and an imaging point of the X-ray generated from the point TG2 in FIG. 2A is smaller than a distance DB between an imaging point of the X-ray generated from the point TG1 and an imaging point of the X-ray generated from the point TG2 in FIG. 2B. Accordingly, the image formed at the point OP1 of FIG. 2A is sharper than the image formed at the point OP2 of FIGS. 2B.

Since the focal spot size of an X-ray used for X-ray imaging is smaller, the sharpness of an X-ray image obtained by the X-ray passing through a certain point on an X-ray emission path being condensed on an X-ray detection surface can be increased, that is, blurring can be reduced, and additionally the image resolution can be increased. Thus, in this preferred embodiment, a configuration which will be describe in detail below is provided, and thereby the focal spot size of an X-ray beam radiated to an imaging region is reduced as small as possible to thereby increase the sharpness of an X-ray image and improve the image resolution.

1.2. Configuration and Function

Figure 3:
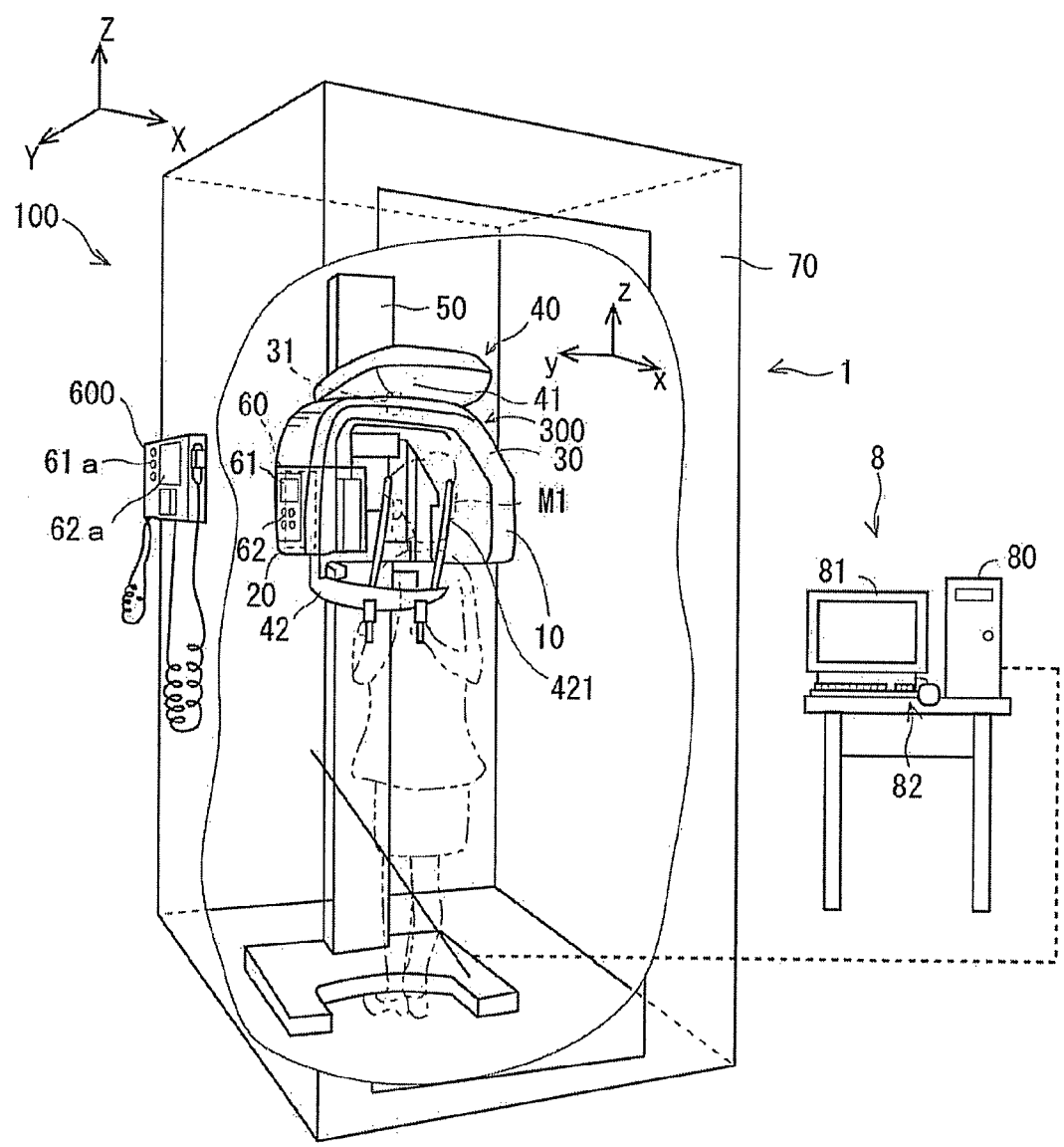
FIG. 3 shows an outline of an X-ray imaging apparatus according to the first preferred embodiment.

FIG. 3 shows an outline of an X-ray imaging apparatus 100 according to a first preferred embodiment. The X-ray imaging apparatus 100 of this preferred embodiment is an X-ray imaging apparatus for medical applications, and radiates an X-ray beam BX to an object M1 fixed at a predetermined position. In the X-ray imaging apparatus 100, various types of X-ray imaging, namely, X-ray CT imaging, panoramic imaging, and cephalo imaging, can be performed based on an input operation made by an operator.

The X-ray CT imaging apparatus 100 mainly includes a main body unit 1 and an information processing device 8. The main body unit 1 performs the X-ray imaging, and collects projection data. The information processing device 8 processes the projection data collected by the main body unit 1, and generates various images.

The main body unit 1 includes an X-ray generation part 10, an X-ray detection part 20, a support part 300, an elevator part 40, a support column 50, and a main-body control part 60. The X-ray generation part 10 emits an X-ray beam BX1 having an X-ray flux toward the object M1. The X-ray detection part 20 detects the X-ray emitted by the X-ray generation part 10. The support part 300 supports each of the X-ray generation part 10 and the X-ray detection part 20. The elevator part 40 is operable to be moved up and down in the vertical direction. The support column 50 extends in the vertical direction. The main-body control part 60 controls operations of the respective parts of the main body unit 1.

In an illustrated example, the support part 300 is configured as a revolving arm 30 which revolves around a revolution shaft 31. However, the support part 300 is not particularly limited to an arm, but various configurations may be conceivable. For example, it may be acceptable that the X-ray generation part 10 and the X-ray detection part 20 arranged opposed to each other are provided on an annular or disk member which rotates around the center of an annular circle.

The X-ray generation part 10 and the X-ray detection part 20 are fixed to both end portions of the revolving arm 30 in a suspended manner. The X-ray generation part 10 and the X-ray detection part 20 are supported so as to be opposed to each other. The revolving arm 30 is fixed to the elevator part 40 in a suspended manner, via the revolution shaft 31 extending in the vertical direction.

The revolving arm 30 revolves to cause the X-ray generation part 10 and the X-ray detection part 20 opposed to each other with the object M1 interposed therebetween to revolve around the object M1, and more specifically around the head of a subject. Thus, the X-ray imaging is performed. The X-ray generation part 10 and the X-ray detection part 20 revolve around the axis of the revolution shaft 31.

In the following, a direction (here, the vertical direction) extending in parallel with an axial direction of the revolution shaft 31 will be referred to as a "Z-axis direction", and a direction intersecting and perpendicular to the Z-axis will be referred to as an "X-axis direction", and furthermore a direction intersecting and perpendicular to both the X-axis direction and the Z-axis direction will be referred to as a "Y-axis direction". The X-axis and the Y-axis direction may be arbitrarily set. Here, in a state where the subject, that is, the object M1, is positioned in the X-ray CT imaging apparatus 100 and exactly opposed to the support column 50, the left-and-right direction with respect to the subject is defined as the X-axis direction, and the front-and-back direction with respect to the subject is defined as the Y-axis direction. This preferred embodiment assumes that the X-axis direction, the Y-axis direction, and the Z-axis direction are perpendicular to one another.

On the other hand, as for three-dimensional coordinates on the revolving arm 30, a direction along which the X-ray generation part 10 and the X-ray detection part 20 are opposed to each other is defined as a "y-axis direction", a horizontal direction perpendicular to the y-axis direction is defined as an "x-axis direction", and a vertical direction perpendicular to the x-axis direction and the y-axis direction is defined as a "z-axis direction". In this and subsequent preferred embodiments, the Z-axis direction is the same as the z-axis direction. The revolving arm 30 of this preferred embodiment is rotated around the revolution shaft 31 extending in the vertical direction. Accordingly, the xyz orthogonal coordinate system is rotated around the Z-axis (=z-axis) relative to the XYZ orthogonal coordinate system.

As shown in FIG. 3, each of the axial directions will be described as the following directions.

In the y-axis direction, a direction extending from the X-ray generation part 10 toward the X-ray detection part 20 is defined as the (+) direction (positive direction), and the direction opposite thereto is defined as the (−) direction (negative direction).

In the x-axis direction, when viewed along the direction extending from the X-ray generation part 10 toward the X-ray detection part 20, the rightward direction is defined as the (+) direction, and the direction opposite thereto is defined as the (−) direction.

In the z-axis direction, the vertically upward direction is defined as the (+) direction, and the direction opposite thereto is defined as the (−) direction.

The elevator part 40 is engaged with the support column 50 provided so as to stand and extend along the vertical direction. In the elevator part 40, an upper frame 41 and a lower frame 42 protrude toward the side opposite to where the elevator part 40 is engaged with the support column 50. Thus, the elevator part 40 has a substantially U-shaped structure.

An upper end portion of the revolving arm 30 is mounted to the upper frame 41. In this manner, the revolving arm 30 is suspended from the upper frame 41 of the elevator part 40, and a movement of the elevator part 40 along the support column 50 causes the revolving arm 30 to move up and down.

The lower frame 42 has an object holding part 421 including an ear rod for fixing the object M1 (here, a human head) from the left and right sides, a chin rest for fixing a chin, and the like. The revolving arm 30 is moved up and down in accordance with the height of the object M1, and set at an appropriate position, and in this condition, the object M1 is fixed by the object holding part 421.

As shown in FIG. 3, the X-ray generation part 10, the X-ray detection part 20, the revolving arm 30, and the elevator part 40 are accommodated in an X-ray shield room 70. An operation display part 600 is provided to an outside wall of the X-ray shield room 70. The operation display part 600 has a display part 61 configured as a liquid crystal monitor or the like, and a operation panel 62 including various buttons. The operation panel 62 is also used for designating the position of an imaging area of a living organ or the like, for example.

The information processing device 8 transmits and receives various data to and from the main body unit 1 by using a communication cable. However, transmission and reception of data between the main body unit 1 and the information processing device 8 may be implemented by wireless means. The information processing device 8 includes an information-processing main body 80 configured as a computer, a work station, or the like. The information-processing main body 80 appropriately processes the projection data acquired by the main body unit 1, and generates data corresponding to each imaging mode. For example, in a case of an X-ray CT imaging mode, three-dimensional data (volume data) expressed by voxels is recreated from the projection data.

A display part 81 including a display device such as a liquid crystal monitor, and an operation part 82 including an input device such as a keyboard, a mouse and the like, are connected to the information-processing main body 80. An operator is allowed to give various commands to the information processing device 8 through the operation part 82. The display part 81 may be configured as a touch panel, too. In such a case, the display part 81 serves a part or the whole of the functions of the operation part 82.

A cephalostat used for cephalo imaging may be provided at an end of an arm fixed to the elevator part 40, though not shown. To be specific, a cephalostat disclosed in Japanese Patent Application Laid-Open No. 2003-245277 may be adopted, for example. Such a cephalostat includes, for example, a fixture for fixing a head at a predetermined position and an X-ray detector used for cephalo imaging.

It is not always necessary that the X-ray detection part 20 and the X-ray generation part 10 are arranged at the same level in the axial direction of the revolution shaft 31. In the X-ray imaging apparatus 100 shown in FIG. 3, the X-ray detection part 20 is arranged at a position slightly higher than the position of the X-ray generation part 10 in the axial direction of the revolution shaft 31.

This arrangement enables the X-ray detection part 20 to approach the head without being brought into contact with a shoulder of the object M1. Even when the revolving arm 30 is revolved in a state where the X-ray detection part 20 is brought closer to the head of the object M1, the X-ray detection part 20 is not brought into contact with a shoulder portion of the object M1.

In the X-ray imaging apparatus 100 shown in FIG. 3, the center CB of the X-ray flux shown in FIG. 1A is radiated toward the X-ray detection part 20 arranged at a position slightly higher than the X-ray generation part 10 so as to be launched in a direction of a vector obtained by summing the +y direction vector and the +z direction vector in the xyz orthogonal coordinate system whose z-axis direction is the direction parallel to the axial direction of the revolution shaft 31.

Figure 4:
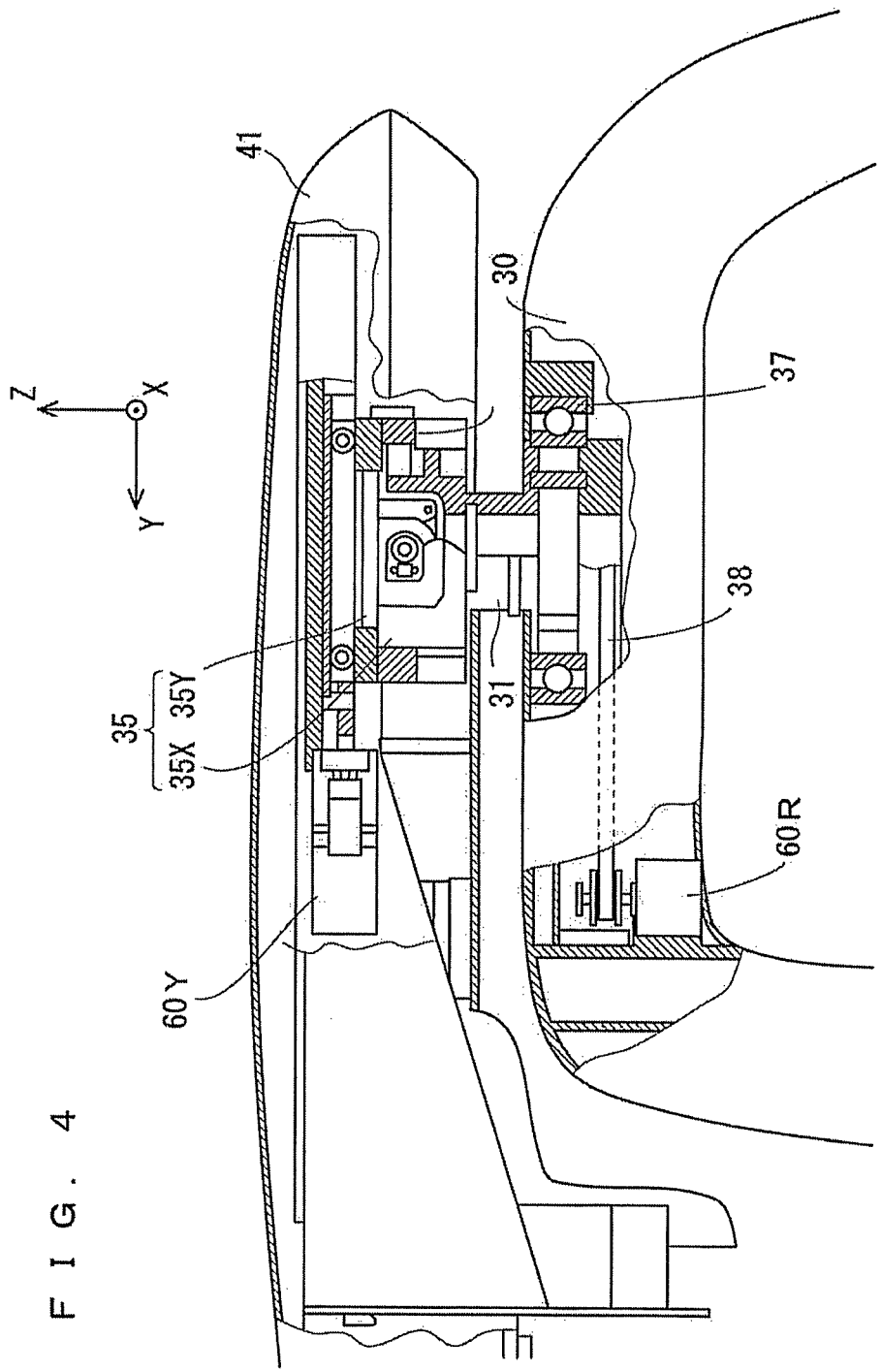
FIG. 4 is a cross-sectional view showing part of a revolving arm and an upper frame, with an internal structure thereof.
Figure 5:
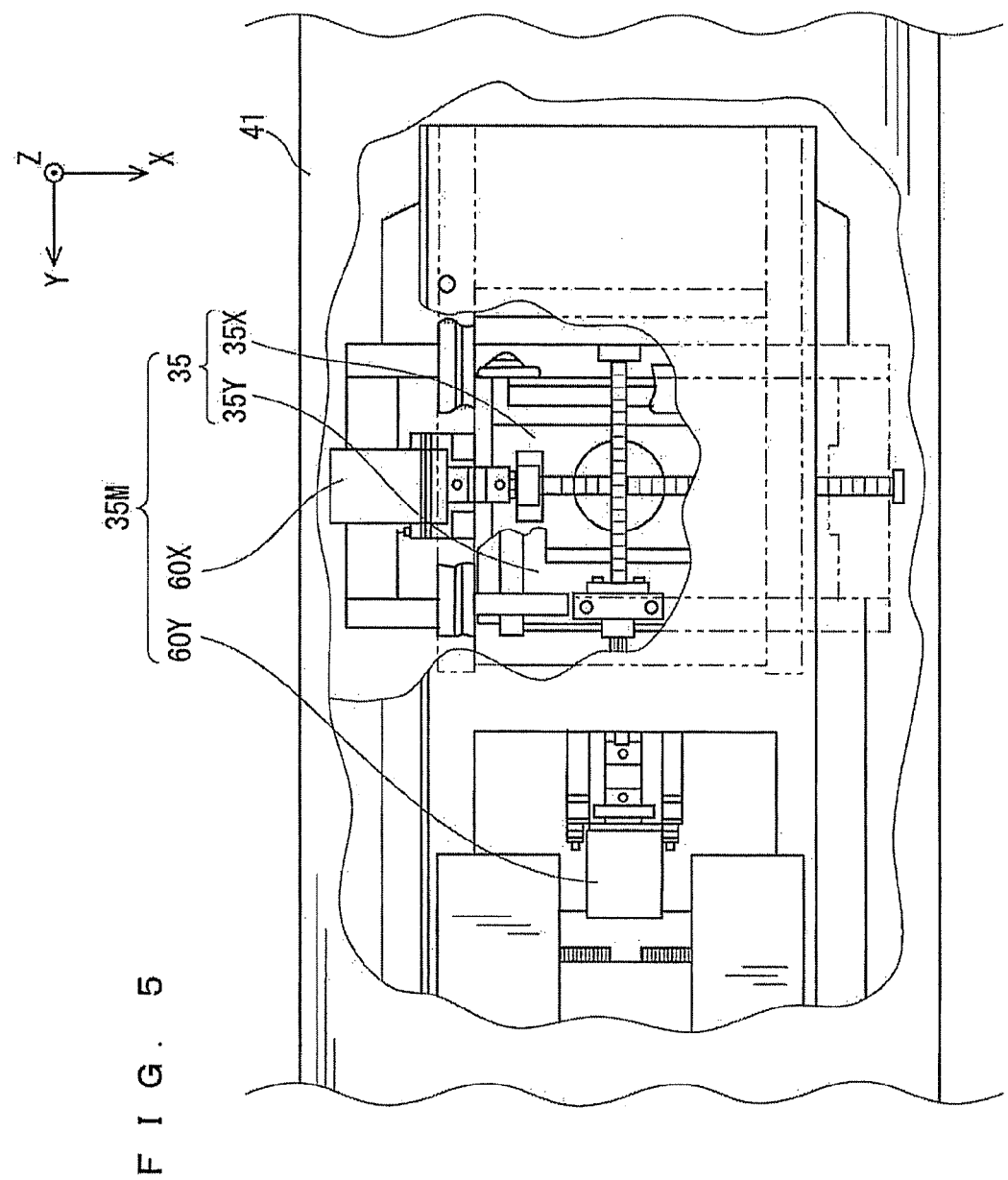
FIG. 5 is a cross-sectional view showing part of the upper frame, with an internal structure thereof.

FIG. 4 is a cross-sectional view showing part of the revolving arm 30 and the upper frame 41, with an internal structure thereof. FIG. 5 is a cross-sectional view showing part of the upper frame 41, with an internal structure thereof. FIG. 4 shows the revolving arm 30 and the upper frame 41 when the X-ray CT imaging apparatus 100 is viewed from a lateral side. FIG. 5 shows the upper frame 41 when the X-ray CT imaging apparatus 100 is viewed from the top side.

The upper frame 41 has a table 35 including an Y-table 35Y and an X-table 35X. The Y-table 35Y moves the revolving arm 30 in the front-and-back direction (Y-axis direction). The X-table 35X is supported on the Y-table 35Y and moved in the lateral direction (X-axis direction). The upper frame 41 also has an Y-axis motor 60Y for driving the Y-table 35Y, an X-axis motor 60X for moving the X-table 35X in the X direction relative to the Y-table 35Y, and a revolving motor 60R for revolving the revolving arm 30 around the revolution shaft 31 which couples the X-table 35X and the revolving arm 30 with each other. Although in this preferred embodiment, the revolution shaft 31 extends along the vertical direction, the revolution shaft may be inclined at an arbitrary angle with respect to the vertical direction. For example, the revolution shaft 31 may be set horizontally, and the object holding part 421 may be configured as a bed on which a patient is placed in a horizontal manner. The table 35, the Y-axis motor 60Y, the X-axis motor 60X function as a two-dimensional movement mechanism 35M which can freely move the revolution shaft 31 in a two-dimensional plane defined by the X-axis direction and the Y-axis direction.

A bearing 37 is provided between the revolution shaft 31 and the revolving arm 30, to allow the revolving arm 30 to be easily rotated around the revolution shaft 31. The revolving motor 60R is fixed inside the revolving arm 30, and transmits rotational force to the revolution shaft 31 through a belt 38, thereby revolving the revolving arm 30. The revolution shaft 31, the bearing 37, the belt 38, and the revolving motor 60R are shown as an example of a revolving mechanism for revolving the revolving arm 30, and the revolving mechanism of the revolving arm 30 is not limited thereto.

In the X-ray CT imaging apparatus 100, the X-axis motor 60X, the Y-axis motor 60Y, and the revolving motor 60R are driven in accordance with a prescribed program, and thereby the X-table 35X and the Y-table 35Y can be moved frontward and backward (in the Y direction), and leftward and rightward (in the X direction) while revolving the revolving arm 30.

[X-Ray Generation Part 10]

Figure 6:
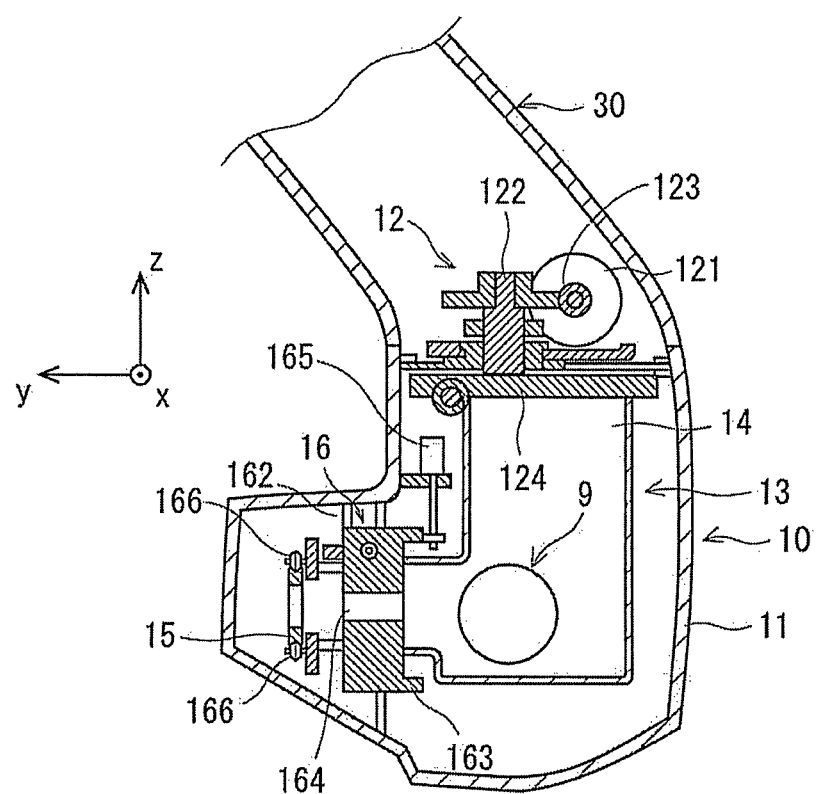
FIG. 6 shows a vertical cross-section of an X-ray generation part.
Figure 7:
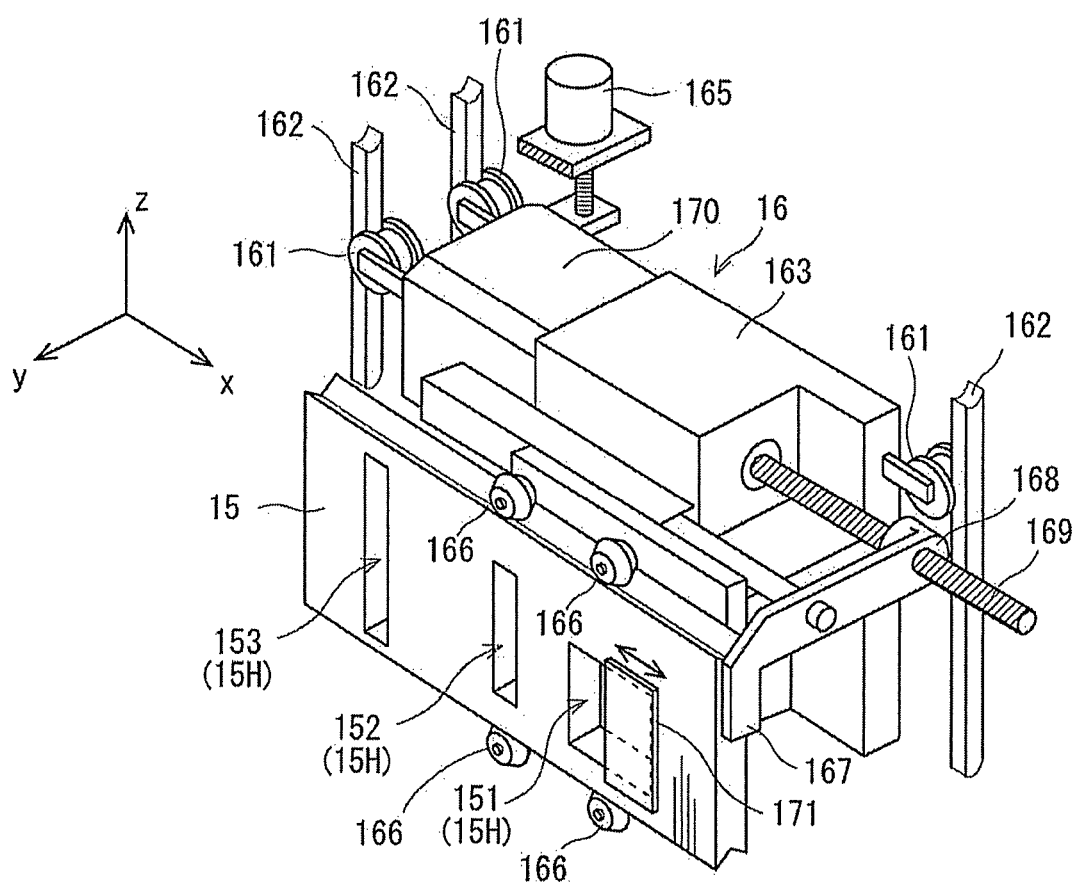
FIG. 7 is a perspective view showing a beam shaping mechanism.

FIG. 6 shows a vertical cross-section of the X-ray generation part 10. FIG. 7 is a perspective view showing a beam shaping mechanism 16. As shown in FIG. 6, the X-ray generation part 10 has a housing 11 for accommodating the respective parts of the X-ray generation part 10. The housing 11 is coupled with the revolving arm 30 via a rotating mechanism 12.

The rotating mechanism 12 has a rotating motor 121 fixed inside the revolving arm 30, a vertical axis 122 fix to the revolving arm 30, a gear mechanism 123 coupling the rotating motor 121 and the vertical axis 122 with each other, a housing 11, and a fixing member 124 fixed to the vertical axis 122.

The housing 11 is rotatable around the vertical axis 122 in a horizontal plane by driving of the rotating motor 121 which is operated based on a control signal supplied from the main-body control part 60 described later.

An X-ray generator 13 is accommodated in the housing 11. The X-ray generator 13 is, except a portion thereof (at the (+y) side in FIG. 6) opposed to the X-ray detection part 20, covered with an X-ray shield casing 14. In the X-ray shield casing 14, a beam-shaping plate 15 is provided in a region opposed to the X-ray detection part 20. The beam-shaping plate 15 is attached to the beam shaping mechanism 16.

The X-ray tube 9 is accommodated in the X-ray shield casing 14.

It may also be acceptable that the housing of the revolving arm 30 and the housing 11 of the X-ray generation part 10 are formed in one piece and coupled with the revolving arm 30 through the rotating mechanism 12 so that the X-ray generator 13 is rotated by the rotating mechanism 12 within the housing 11.

As shown in FIG. 7, the beam shaping mechanism 16 has a block 163 supported in such a manner that the block 163 can be moved up and down along a plurality of vertical guide rails 162 with a plurality of guide rollers 161 interposed therebetween. The block 163 has an X-ray passing hole 164 (see FIG. 6) for guiding the X-ray emitted from the X-ray generator 13 toward the X-ray detection part 20.

The block 163 is coupled with an elevation motor 165 fixed to the housing 11, through a screw mechanism. By driving the elevation motor 165, the X-ray generation part 10 can move an X-ray radiation angle in the Z-axis direction. This enables the X-ray radiation angle to be moved up and down without moving the X-ray generation part 10 up and down. Due to this configuration, the X-ray CT imaging of a desired region can be performed by, for example, moving up and down the angle of radiation of an X-ray cone beam while a beam passing hole 151 which will be described later is being placed in front of the X-ray passing hole 164. At this time, as a detection surface of the X-ray detector 21, there is appropriately adopted a detection surface having such upper and lower widths as to allow a detection of an X-ray cone beam in either case where the direction of radiation of the X-ray cone beam is upward or downward.

The beam-shaping plate 15 is provided at the front side (outside the X-ray passing hole 164) of the block 163. The beam-shaping plate 15 shapes the X-ray beam emitted from the X-ray generator 13, and has a plurality of openings for the X-ray to pass therethrough. The beam-shaping plate 15 serves as a restriction part for restricting the radiation range. The beam-shaping plate 15 is supported by a plurality of guide rollers 166 fixed to a front surface of the block 163 in such a manner that the beam-shaping plate 15 can be moved in the horizontal direction (X-axis direction).

A coupling arm 167 is coupled with one end of the beam-shaping plate 15. A nut 168 is attached to the coupling arm 167. The block 163 rotatably supports a screw shaft 169 extending in a longitudinal direction of the beam-shaping plate 15. The nut 168 is threadably engaged with the screw shaft 169, and the screw shaft 169 is coupled with a motor 170 fixed to the block 163.

By driving of the motor 170 which is operated based on a control signal supplied from the main-body control part 60, the beam-shaping plate 15 is moved at a front portion of the block 163 in one direction of the horizontal direction, that is, in a direction intersecting the X-ray beam.

In this preferred embodiment, the beam-shaping plate 15 has three types of opening portions 15H which allow the X-ray to pass therethrough. The X-ray pass-through opening (primary slit, collimator) having these three types of opening portions includes a beam passing hole 151 for CT imaging, a beam passing hole 152 for cephalo imaging, and a beam passing hole 153 for panoramic imaging. The beam passing hole 151 for CT imaging has a rectangular or square shape for shaping the X-ray beam into a cone (including a pyramid). The beam passing hole 152 for cephalo imaging is elongated in the vertical direction for forming a narrow beam by shaping the X-ray beam into an elongated band. The beam passing hole 153 for panoramic imaging is also elongated.

In a case where, for example, the beam passing hole 151 for CT imaging is opposed to the X-ray generator 13, an X-ray cone-beam is emitted from the X-ray generation part 10 so as to spread in the form of a truncated pyramid toward the X-ray detection part 20. When the longitudinal length and the horizontal length of the beam passing hole 151 for CT imaging are equal to each other, a cross-sectional surface of the X-ray beam as sectioned perpendicularly to an X-ray traveling direction has a substantially square shape.

In a case where the beam passing hole 152 for cephalo imaging or the beam passing hole 153 for panoramic imaging is opposed to the X-ray generator 13, an X-ray beam having a substantially flat-plate shape (more strictly, a truncated pyramid) and having a vertically-elongated cross-sectional surface is emitted from the X-ray generation part 10 toward the X-ray detection part 20.

Various configurations including a conventional one may be adopted as the structure of a cephalo-imaging apparatus in which a cephalostat used for cephalo imaging is provided at an end of a cephalo arm fixed to the elevator part 40. In a specific example, the structure disclosed in FIG. 8 of Japanese Patent Application Laid-Open No. 2003-245277 filed by the applicant of the present application may be adopted as appropriate.

A blocking plate 171 is provided on a front surface of the beam-shaping plate 15. The blocking plate 171 is moved in the horizontal direction to partially block the opening of the beam passing hole 151. The blocking plate 171 is connected to a horizontal movement mechanism (not shown), and movable in the horizontal direction relative to the beam-shaping plate 15. The beam shaping mechanism 16 moves the blocking plate 171 in the horizontal direction based on a control signal supplied from the main-body control part 60, to thereby partially block the X-ray passing through the beam passing hole 151. Thus, the spread (width) of the X-ray beam in the horizontal direction is adjusted and restricted. This function of restricting the passing of the X-ray is used in a case of performing a mode for imaging a relatively small range in X-ray CT imaging. As described above, in this preferred embodiment, the beam shaping mechanism 16 forms a restriction part for restricting the passing of the X-ray radiation.

The opening degree of the spread of the X-ray cone-beam in the horizontal direction may be adjusted by the blocking plate 171. However, it may also possible that the width of the X-ray passing hole 164 of the block 163 in the horizontal direction is made equal to the width of the beam passing hole 151 in the horizontal direction, and the opening degree of the spread of the X-ray cone-beam in the horizontal direction is adjusted by the beam-shaping plate 15 being moved by driving of the motor 170.

The beam-shaping plate 15 is displaceable relative to the block 163 such that the beam passing hole 151 of the beam-shaping plate 15 can be brought into a position overlapping the X-ray passing hole 164 to provide no obstacle to the X-ray passing through the X-ray passing hole 164. In this case, the X-ray cone-beam is radiated with a maximum spread width in the horizontal direction.

The beam-shaping plate 15 is displaceable relative to the block 163 such that the beam passing hole 151 of the beam-shaping plate 15 can be brought into a position for restricting the X-ray passing through the X-ray passing hole 164. In this case, the X-ray cone-beam is radiated with a restricted spread width as compared with the maximum spread width in the horizontal direction.

The opening degree of the spread of the X-ray cone-beam in the horizontal direction is determined by controlling the position of the beam-shaping plate 15.

The beam passing hole 151 and the X-ray passing hole 164 are shown as an exemplary opening for partially blocking the passing of the X-ray.

A sub beam-shaping plate may be separately provided at the front or back side of the beam-shaping plate 15, though not shown. The sub beam-shaping plate can be driven in the same direction as the moving direction of the beam-shaping plate 15, by another drive motor similar to the drive motor 170 for driving the beam-shaping plate 15. As a guide mechanism such as a guide roller, the ones similar to the guide roller 166 can be adopted.

In a specific example, the structure of an X-ray narrowing device disclose in FIGS. 3 and 4 of Japanese Utility Model Publication No. 7-15524 (1995) which is the application filed by the applicant of the present application may be adopted. In the X-ray narrowing device, an X-ray is restricted by overlap of a plurality of mask plates 4 and 5.

A beam passing hole is provided also in the sub beam-shaping plate. The width of the beam passing hole of the sub beam-shaping plate in the horizontal direction is made equal to or larger than the width of the beam passing hole 151 of the beam-shaping plate 15 in the horizontal direction, and the sub beam-shaping plate is displaceable relative to the beam-shaping plate 15.

The sub beam-shaping plate is displaceable relative to the beam-shaping plate 15 such that the beam passing hole of the sub beam-shaping plate can be brought into a position overlapping the beam passing hole 151 to provide no obstacle to the X-ray passing through the beam passing hole 151 of the beam-shaping plate 15. In this case, the X-ray cone-beam is radiated with the maximum spread width in the horizontal direction.

The sub beam-shaping plate is displaceable relative to the beam-shaping plate 15 such that the beam passing hole of the sub beam-shaping plate can be brought into a position for restricting the X-ray passing through the beam passing hole 151 of the beam-shaping plate 15. In this case, the X-ray cone-beam is radiated with a restricted spread width as compared with the maximum spread width in the horizontal direction.

The angle and the position of the spread of the X-ray cone-beam in the horizontal direction is determined by controlling the position of the beam-shaping plate 15 and the position of the sub beam-shaping plate relative to each other.

The shape of the beam passing hole 151 for CT imaging is not limited to a rectangular or square shape, but any shape is adoptable. For example, the beam passing hole 151 may be formed into a circular shape to form the imaging region into a spherical shape.

[X-Ray Detection Part 20]

Figure 8:
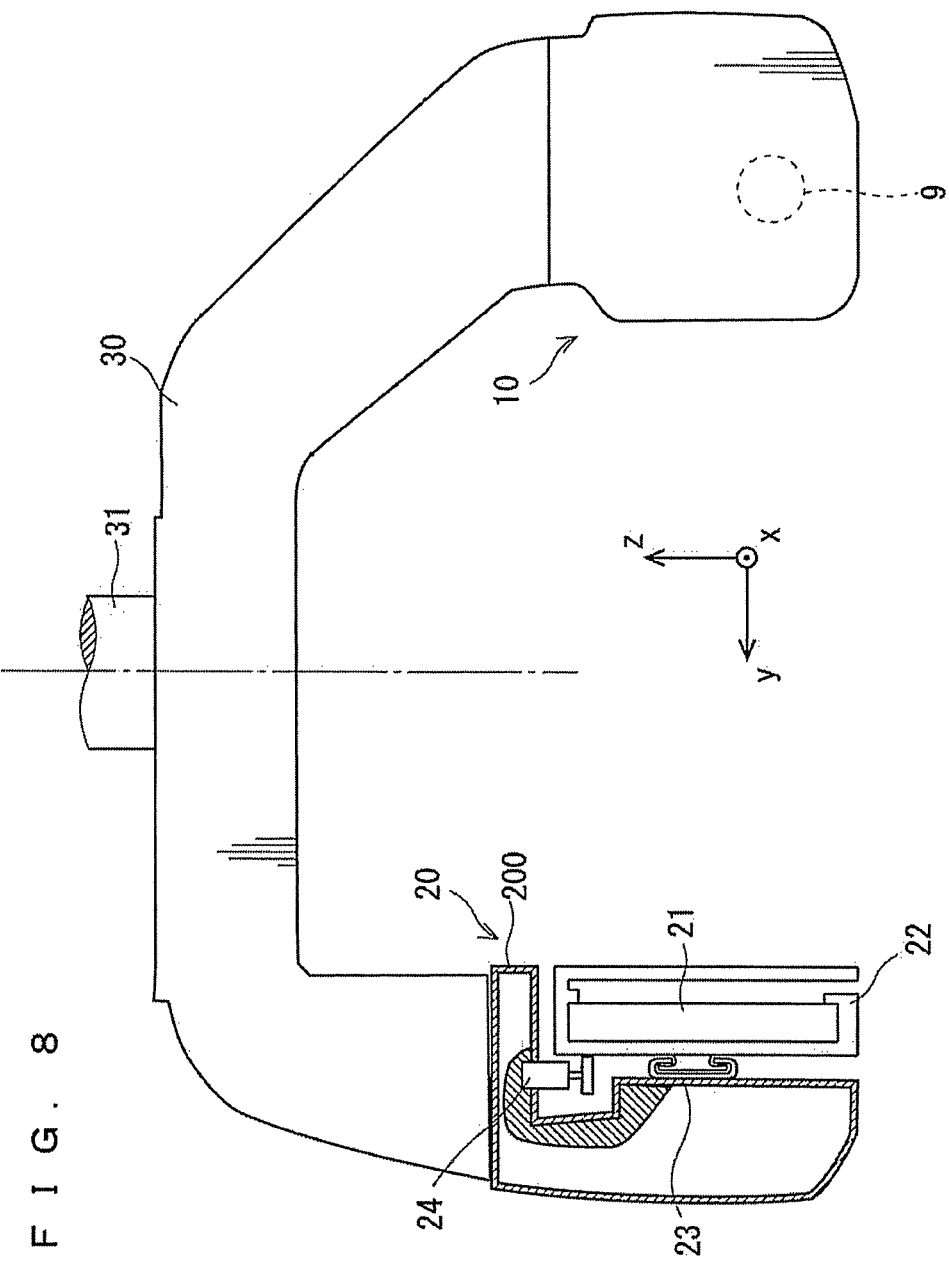
FIG. 8 is a front elevational view showing the revolving arm.

FIG. 8 is a front elevational view showing the revolving arm 30. In FIG. 8, an internal structure of the X-ray detection part 20 is partially shown. The X-ray detection part 20 has a housing 200 for accommodating respective parts of the X-ray detection part 20.

An X-ray detector 21, a detector holder 22, a guide rail 23, and a movement motor 24 are provided in the housing 200. The X-ray detector 21 detects the X-ray. The detector holder 22 holds the X-ray detector 21 therein. The guide rail 23 supports the detector holder 22 so as to be slidably movable in the horizontal direction. The movement motor 24 is mounted to the housing 200.

The X-ray detector 21 includes an X-ray sensor having a detection surface which is formed by semiconductor imaging elements being arranged in a plane two-dimensionally in a longitudinal direction and a lateral direction. The semiconductor imaging element is a detection element for detecting an X-ray. As the X-ray sensor, for example, an X-ray sensor such as an MOS sensor and a CCD sensor is conceivable. However, this is not limitative, and various types can be used including a flat-panel detector (FPD) such as a CMOS sensor, an X-ray image intensifier (XII), other solid-state imaging elements, and the like.

The detector holder 22 is in contact with a roller attached to a rotation shaft of the movement motor 24. The detector holder 22 is driven by the movement motor 24 which is operated based on a control signal supplied from the main-body control part 60, to be moved in the horizontal direction along the guide rail 23.

The detector holder 22 is in contact with a roller attached to a rotation shaft of the movement motor 24. The detector holder 22 is driven by the movement motor 24 which is operated based on a control signal supplied from the main-body control part 60, to be moved in the horizontal direction along the guide rail 23.

FIG. 9 is a perspective view showing the detector holder 22. The detector holder 22 has beam passing holes (secondary shaping slit, collimator) 221, 222 at the side opposed to the X-ray generation part 10. The shapes of the beam passing holes 221, 222 correspond to the shapes of the above-described beam passing holes 151, 153, respectively. For example, the X-ray beam passing through the beam passing hole 151 is shaped by the beam passing hole 221 with an increased accuracy, and projected to the X-ray detector 21.

The member in which the beam passing holes (secondary shaping slit, collimator) 221, 222 are provided may be omitted.

The X-ray detector 21 has a detection element group 211 and a detection element group 212. The detection element group 211 is formed by the imaging elements being arranged in a rectangular or square shape corresponding to the beam passing hole 151 having a rectangular or square shape. The detection element group 212 is formed by the imaging elements being arranged in a vertically-elongated shape corresponding to the beam passing hole 153 having a vertically-elongated shape. The X-ray detector 21 is inserted into a slot 224 formed by the detector holder 22.

In a state where the X-ray detector 21 is set in the slot 224, the detection element group 211 having a substantially square shape is placed in a position behind the beam passing hole 221 having a substantially square shape, and the detection element group 212 is placed in a position behind the beam passing hole 222.

The detector holder 22 is controlled such that the detection element group 211 is brought into a position irradiated with the X-ray having passed through the beam passing hole 151 in the X-ray CT imaging, and the detection element group 212 is brought into a position irradiated with the X-ray having passed through the beam passing hole 153 in the panoramic imaging.

Although in this preferred embodiment, the detection element groups 211, 212 are provided in the X-ray detector 21, only the detection element group 211 may be provided in the X-ray detector 21 so that only the selection between the beam passing hole 151 and the beam passing hole 153 is performed and the X-ray is detected by the single detection element group 211 in both of the X-ray CT imaging and the panoramic imaging. At this time, control of only the elements included in a range irradiated with the X-ray allows an image signal to be transmitted with an increased efficiency.

It may be also acceptable that the detection element groups 211, 212 are provided on different X-ray detectors 21, respectively, and a plurality of X-ray detectors 21 are replaced.

Figure 10:
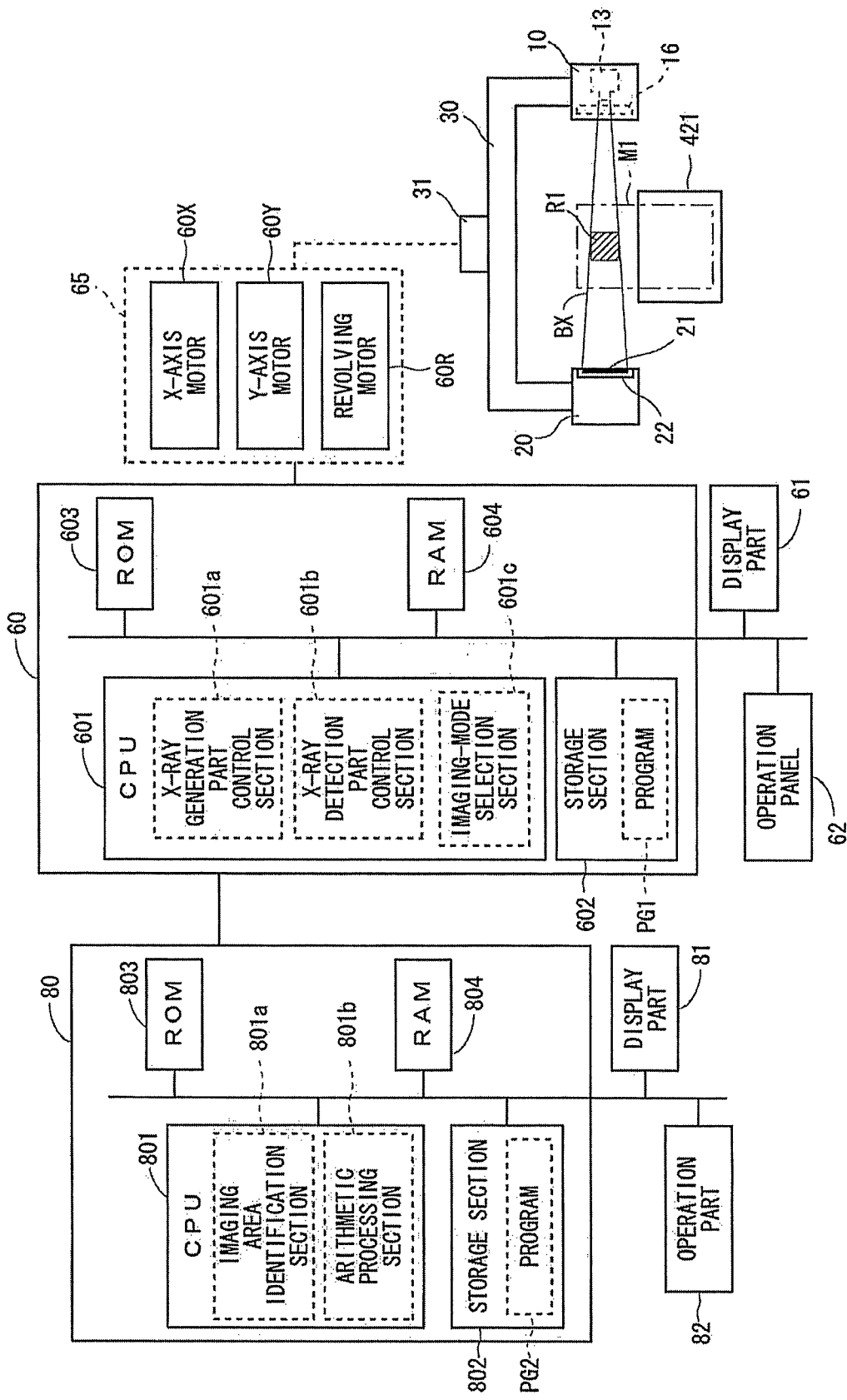
FIG. 10 is a block diagram showing a configuration of an X-ray CT imaging apparatus.

FIG. 10 is a block diagram showing a configuration of the X-ray CT imaging apparatus 100. As shown in FIG. 10, the revolving motor 60R, the X-axis motor 60X, and the Y-axis motor 60Y form a driving section 65 serving as a driving source for moving the revolving arm 30 relative to the object M1 placed in the predetermined position. The driving section 65 and the object holding part 421 function as a movement mechanism for moving the X-ray generation part 10 including the X-ray generator 13 and the X-ray detection part 20 including the X-ray detector 21 relative to the object M1. The driving section 65 is an example of a revolving (revolution) drive mechanism which drives the revolving arm 30 in a revolving manner, by using the revolving motor 60R as a main element.

Here, a configuration for revolving the X-ray generation part 10 and the X-ray detection part 20 relative to the object M1 in a case of the X-ray CT imaging will be mentioned.

A configuration for revolving the X-ray generation part 10 and the X-ray detection part 20 relative to the object M1 in a case of the X-ray CT imaging is not limited to the one which revolves the revolving arm 30 around the revolution shaft 31 while fixing the revolution shaft 31 in a particular position.

In the X-ray CT imaging, the revolution shaft 31 is moved to a particular position in a two-dimensional plane (here, the horizontal plane) by the X-table 35X and the Y-table 35Y, and then the revolution shaft 31 is fixed in this position. Then, the revolving arm 30 is revolved around the revolution shaft 31, and thereby the X-ray generation part 10 and the X-ray detection part 20 can be rotated. In this case, the position of the rotation axis of the X-ray generation part 10 and the X-ray detection part 20 is coincident with the position of the revolution shaft 31.

In the X-ray CT imaging, furthermore, while the revolution shaft 31 is moved in the two-dimensional plane by driving of the X-table 35X and the Y-table 35Y, the revolving arm 30 can be simultaneously revolved around the revolution shaft 31. By a combined motion of the movement of the revolving arm 30 in the horizontal plane caused by the movement of the revolution shaft 31 and the revolution of the revolving arm 30 around the revolution shaft 31, the X-ray generation part 10 and the X-ray detection part 20 can be rotated around a particular rotation axis which is set in a position different from the position of the revolution shaft 31. As an example of setting a rotation axis of the X-ray generation part 10 and the X-ray detection part 20 to be a position different from the position of the mechanical revolution shaft 31, the structure of the X-ray CT imaging apparatus disclosed in Japanese Patent Application Laid-Open No. 2007-29168 can be applied as appropriate.

The main-body control part 60 has a configuration of a general computer, in which a CPU 601, a storage section 602, a ROM 603, and a RAM 604 are connected to a bus line. The CPU 601 executes a program PG1 including a control program for controlling the driving section 65 and a control program for controlling an operation of the X-ray generation part 10 and the X-ray detection part 20. The storage section 602 is formed as a fixed disk such as a hard disk, and stores therein various data and the program PG1.

The CPU 601 executes, on the RAM 604, the program PG1 stored in the storage section 602, and thereby functions as an X-ray generation part control section 601a, an X-ray detection part control section 601b, and an imaging-mode selection section 601c. The X-ray generation part control section 601a controls the X-ray generation part 10, the X-ray detection part control section 601b controls the X-ray detection part 20, and the imaging-mode selection section 601c selects an imaging mode, in accordance with various imaging modes. The CPU 601 forming the main-body control part 60 and a CPU 801 forming the information-processing main body 80 collectively constitute a single control system.

The operation panel 62 included in the main-body control part 60 has a plurality of operation buttons, and the like. Examples of an input device used in place of or in combination with the operation panel 62 may include not only the operation buttons but also a device such as a keyboard, a mouse, and a touch pen. It may be also acceptable to receive a voice command by a microphone or the like, and recognize it. Thus, the operation panel 62 is one example of operation means. Accordingly, any operation means may be adopted, as long as it can receive an operation made by an operator and communicated it to the CPU 601. The display part 61 may be configured as a touch panel. In such a case, the display part 61 serves a part or the whole of the function of the operation panel 62.

On the display part 61, various information necessary for the operation of the main body unit 1 is displayed in the form of a text, an image, and the like. Here, in a possible configuration, display contents displayed on the display part 81 of the information processing device 8, in FIG. 3, may be displayed on the display part 61, too. Additionally, in a possible configuration, various commands may be transmitted to the main body unit 1 through a pointer operation being performed on the text or the image displayed on the display part 61 by using a mouse or the like.

In accordance with a command inputted to the operation panel 62 or the information processing device 8 by the operator, an imaging-mode selection section 601c transmits a selection signal and controls the operations of the respective elements of the main body unit 1, so as to perform a designated imaging modes from various imaging modes including the X-ray CT imaging mode, the panoramic imaging mode, and the cephalo-imaging mode.

The operation and the display concerning the main-body control part 60 may be realized also by the operation display part 600. Although the operation and display functions may be redundantly provided, the operation display part 600 may be configured to perform certain operation and display peculiar thereto. Moreover, a control section may be provided also in the operation display part 600, and the control performed by the main-body control part 60 may be partially assigned to the operation display part 600, or alternatively the function of the main-body control part 60 may be fully provided by the operation display part 600.

In the X-ray CT imaging mode, the X-ray imaging apparatus 100 revolves the revolving arm 30 around the revolution shaft 31 while radiating the pyramid-shaped X-ray beam BX1 (cone-beam) to an imaging region (such as a living organ) of the object M1, in a state where the X-ray generation part 10 and the X-ray detection part 20 are opposed to each other with the object M1 interposed therebetween. In the panoramic imaging mode, the X-ray imaging apparatus 100 revolves the revolving arm 30 around the revolution shaft 31 to move the revolving arm 30 on a predetermined orbit while radiating the elongated X-ray beam BX1 to a living organ (specifically, a jaw bone or the like). In the cephalo-imaging mode, the X-ray imaging apparatus 100 radiates the X-ray from a predetermined direction to the head of the object M1 fixed in a certain position.

The X-ray imaging apparatus 100 performs the various imaging modes as described above, and transmits the projection data acquired by the main body unit 1 to the information processing device 8. The main body unit 1 receives a select command of the imaging mode, coordinate data indicating an imaging position, and the like, from the information processing device 8, and performs the X-ray imaging.

The information-processing main body 80 has a configuration of a general computer, in which the CPU 801 executing various programs, a storage section 802 formed as a fixed disk such as a hard disk and storing therein various data and a program PG2, a ROM 803, and a RAM 804 are connected to a bus line.

The CPU 801 executes, on the RAM 804, the program PG2 stored in the storage section 802, and thereby functions as an imaging area identification section 801a and an arithmetic processing section 801b. The imaging area identification section 801a calculates coordinates of a region designated by the operation part 82, and identifies an imaging region R1. The arithmetic processing section 801b performs arithmetic processing including, for example, reconstruction of three-dimensional data from the projection data.

The programs PG1, PG2 may be acquired by the main-body control part 60 and the information-processing main body 80 via a predetermined network line or the like. Alternatively, the programs PG1, PG2 may be stored in a portable medium (such as a CD-ROM) and acquired by a predetermined reader reading it.

In this preferred embodiment, the imaging region is designated by the operator operating the operation panel 62 or the operation part 82. To be more specific, a screen (an illustration, a panoramic image, or the like) displaying a part or the whole of a living body is displayed on the display part 61 or the display part 81, and the operator designates a desired region to be imaged by using the operation panel 62 or the operation part 82, thereby designating a particular imaging region. In another possible configuration, an imaging region may be directly designated based on an input of a code or the name of a region through the operation panel 62 or the operation part 82.

1.3. Operation of X-Ray Imaging Apparatus

Next, an operation of the X-ray imaging apparatus 100 will be described. The operation of the X-ray imaging apparatus 100 described below is, if not otherwise specified, controlled by the main-body control part 60 or the information-processing main body 80.

Figure 11:
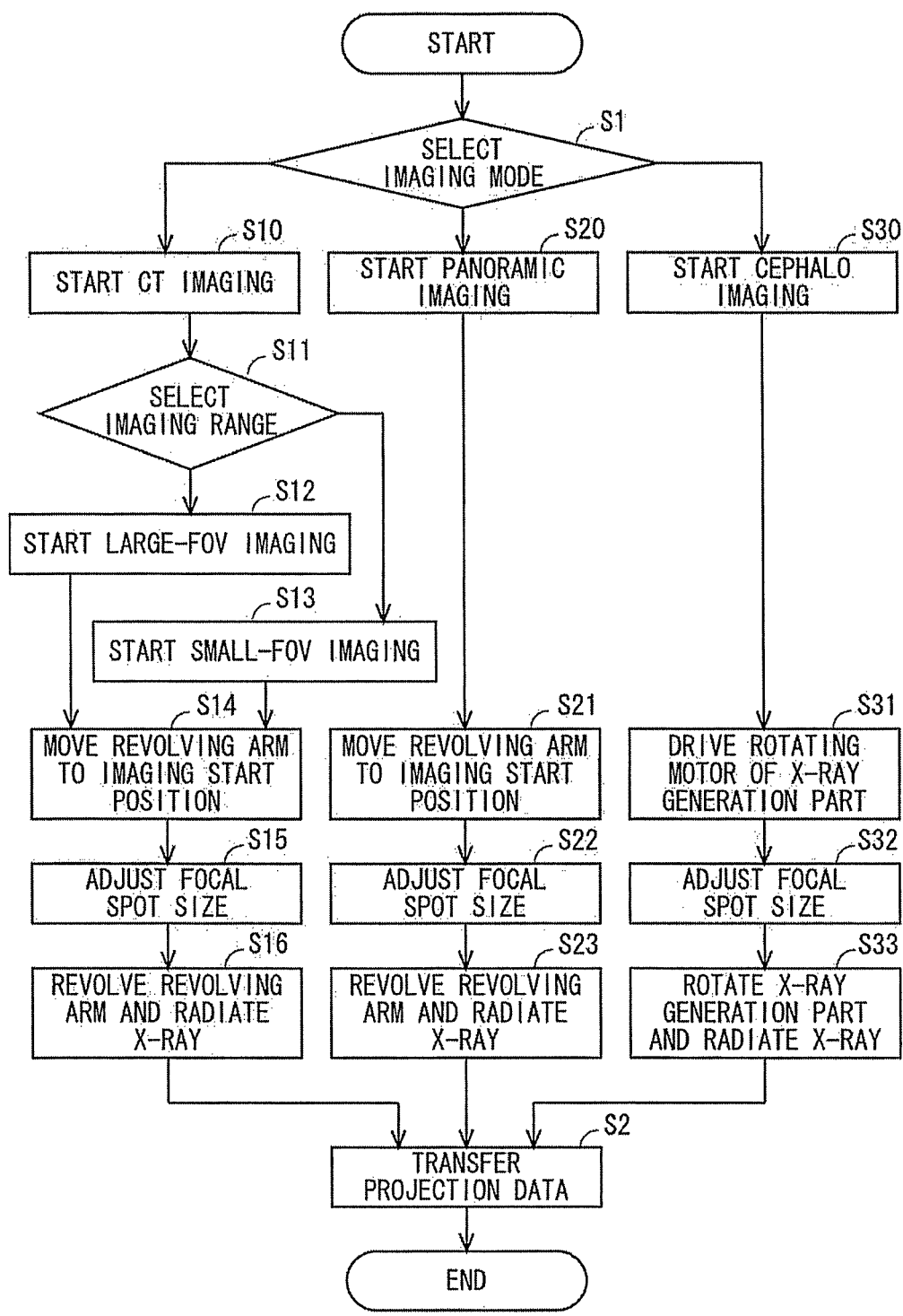
FIG. 11 is a flow chart showing an operation of the X-ray imaging apparatus.

FIG. 11 is a flow chart showing an operation of the X-ray imaging apparatus 100. In the X-ray imaging apparatus 100, firstly, the imaging mode is selected (step S1). As described above, the X-ray imaging apparatus 100 can perform the X-ray CT imaging, the panoramic imaging, and the cephalo imaging. In step S1, any of the imaging modes is selected. In accordance with the imaging mode selected in step S1, the X-ray imaging apparatus 100 is brought into each of the X-ray CT imaging mode (step S10), the panoramic imaging mode (step S20), and the cephalo-imaging mode (step S30).

In the X-ray CT imaging mode (step S10), the X-ray imaging apparatus 100 selects the imaging range (step S11). More specifically, a designation screen for the designation of an imaging range is displayed on the display part 61 or the display part 81, and the operator designates an imaging range through operation means (the operation panel 62 or the operation part 82) while watching the screen. Based on this designation, the X-ray imaging apparatus 100 selects the imaging range.

In step S11, when a relatively large region is selected as the imaging region, the X-ray imaging apparatus 100 starts operating a large-FOV imaging mode (step S12). On the other hand, when a small imaging region is selected, the X-ray imaging apparatus 100 start operating a small-FOV imaging mode (step S13).

In step S12 or step S13, the X-ray imaging apparatus 100 performs a corresponding imaging operation. More specifically, firstly, the revolving arm 30 is moved to a predetermined imaging start position (step S14). Here, positioning is performed such that a relative positional relationship between the imaging region of the object M1, and the X-ray generation part 10 and the X-ray detection part 20 can be set to a positional relationship predefined for X-ray CT imaging.

Then, the focal spot size is adjusted (step S15). More specifically, the beam shaping mechanism 16 having the X-ray restriction part is driven and controlled such that, in a case of the small-FOV imaging mode, an X-ray beam corresponding to a portion of the X-ray beam BX emitted from the X-ray generator 13 which has a smaller focal spot size can be radiated toward the imaging region. Details thereof will be described later.

After the adjustment of the focal spot size is completed, the X-ray imaging apparatus 100 controls the driving section 65 to thereby revolve the revolving arm 30 around the object M1 while radiating the X-ray beam to the imaging region (step S16). Then, the X-ray transmitted through the imaging region is detected by the X-ray detector 21 (specifically, the detection element group 211), and thus projection data of the X-ray is collected.

In a case where the X-ray imaging apparatus 100 is brought into the panoramic imaging mode as a result of the selection made in step S1 (step S20), the revolving arm 30 is moved to a predetermined panoramic imaging start position (step S21). Thereby, a relative positional relationship between the imaging region of the object M1, and the X-ray generation part 10 and the X-ray detection part 20 is set to be a positional relationship predefined for panoramic imaging.

Then, the focal spot size is adjusted (step S22). More specifically, the beam-shaping plate 15 is displaced such that an X-ray corresponding to a portion of the X-ray beam BX1 emitted from the X-ray generator 13 which has a smaller focal spot size can pass through the beam passing hole 152 of the beam-shaping plate 15. Details thereof will be described later.

After the adjustment of the focal spot size is completed, the driving section 65 is controlled to thereby move the revolving arm 30 on a panoramic-imaging orbit while revolving the revolving arm 30 around the object M1, and radiate the X-ray beam obtained after the adjustment of the focal spot size in step S22 to the imaging region (step S23). Then, the X-ray transmitted through the imaging region is detected by the X-ray detector 21 (specifically, the detection element group 212), and thus projection data of the X-ray is collected.

In a case where the X-ray imaging apparatus 100 is brought into the cephalo-imaging mode as a result of the selection made in step S1 (step S30), the rotating motor 121 of the X-ray generation part 10 is driven (step S31). As a result, the X-ray generation part 10 is displaced so as to be oriented in a prescribed direction (step S31). To be more specific, as disclosed in Japanese Patent Application Laid-Open No. 2003-245277 for example, the X-ray generation part 10 is displaced into a position allowing the X-ray to be radiated from the X-ray generation part 10 toward the head of the object M1 fixed to the cephalostat.

Then, the focal spot size is adjusted (step S32). Here, the beam-shaping plate 15 is displaced such that an X-ray corresponding to a portion of the X-ray beam BX1 emitted from the X-ray generator which has a smaller focal spot size can pass through the beam passing hole 152 of the beam-shaping plate 15.

Then, by driving the rotating motor 121, the X-ray generation part 10 is rotated around the vertical axis 122, and in this state the X-ray beam for cephalo imaging is radiated to the imaging region. The X-ray transmitted through the imaging region is detected by the X-ray detector of the cephalostat, and thus projection data of the X-ray is collected.

It is not always necessary to radiate the X-ray beam while rotating the rotating motor 121. After the X-ray generation part is oriented in the prescribed direction, the rotation may be stopped, and the object M1 may be scanned with the X-ray beam while the beam-shaping plate 15 provided on the front surface of the X-ray generator 13 is moved and thus the beam passing hole 152 is moved. That is, the configuration disclosed in Japanese Patent Application Laid-Open No. 2003-245277 filed by the applicant of the present application may be adopted.

Instead of driving the rotating motor 121, the revolving motor 60R may be driven to perform the cephalo imaging while revolving the revolving arm 30.

The projection data of the X-ray collected step S16, step S23, step S33, is transmitted from the main body unit 1 to the information processing device 8 (step S2). The projection data is processed in the information processing device 8, and an X-ray image corresponding to any of various imaging modes is generated. The generated X-ray image is appropriately displayed on the display part 81.

Next, the adjustment of the focal spot size in step S15, step S22, step S32 will be described with reference to FIGS. 12A to 12D. FIGS. 12A to 12D are schematic top views of the X-ray imaging apparatus 100, showing a situation where X-ray imaging according to the first preferred embodiment is performed. FIG. 12A shows a situation where the large/wide-FOV imaging mode is performed, FIG. 12B shows a situation where the small/narrow-FOV imaging mode is performed, and FIG. 12C shows a situation where the panoramic imaging mode is performed. In the present application, the large/wide-FOV imaging mode and the small/narrow-FOV imaging mode are sometimes called a large-radiation-field X-ray CT imaging mode and a small-radiation-field X-ray CT imaging mode, respectively. In each of FIGS. 12A to 12D, a part corresponding to the opening portion 15H in the respective imaging modes is shown in an enlarged view as enclosed in a circle.

In an example of the imaging mode shown in each of FIGS. 12A to 12D, the radiation range of the spread SP shown in FIG. 1A is as follows:

- in the large-radiation-field X-ray CT imaging mode of FIG. 12A, the radiation range is SP1, and the opening width of the opening portion 15H is 15H1;
- in the small-radiation-field X-ray CT imaging mode of FIG. 12B, the radiation range is SP2, and the opening width of the opening portion 15H is 15H2 which is smaller than opening width 15H1; and
- in the panoramic imaging mode of FIG. 12C, the radiation range is SP3, and the opening width of the opening portion 15H is 15H3 which is smaller than opening width 15H2.

In an example shown in FIGS. 12A to 12C, although any of the X-ray beams BX1, BX2, and BX3 is received by the detection surface of the single X-ray detector 21, the X-ray beams BX1, BX2, and BX3 are received in different ranges. The upper and lower widths (the widths in the same direction as the axial direction of the revolution shaft 31) of the detection surface of the X-ray detector 21 are set so as to sufficiently receive at least the X-ray beam BX3 for performing the panoramic imaging.

The radiation ranges SP1, SP2, and SP3 are radiation ranges of X-ray beams BX1, BX2, and BX3, which are similar to the radiation range (spread) SP of the X-ray beam BX as viewed along the line-of-sight direction D of FIG. 1C.

The radiation ranges SP1, SP2, and SP3 are different in size. The radiation range SP1 is the largest, and the radiation range decreases in the order of SP2>SP3. The opening width of the opening portion 15H satisfies the relationship of 15H1>15H2>15H3.

As for the radiation range of the spread SP shown in FIG. 1A, the amount of restriction of the emission range in a portion of the X-ray beam closer to the cathode 91 is as follows:

- in the large-radiation-field X-ray CT imaging mode of FIG. 12A, the amount of restriction is CR1;
- in the small-radiation-field X-ray CT imaging mode of FIG. 12B, the amount of restriction is CR2; and
- in the panoramic imaging mode of FIG. 12C, the amount of restriction is CR3.

Here, as shown in the enlarged view of FIG. 12A, the position of an end portion 15HC of the opening portion 15H at the cathode side is defined as a reference position POS1. Each of the amounts of restriction CR1, CR2, and CR3 is represented as a distance between the end portion 15HC and the reference position POS1 in each of the imaging modes (see the enlarged views in FIG. 12A to 12C). As shown in FIGS. 12A to 12D, as the X-ray radiation range is narrower, the amount of restriction increases. The magnitude relation among the amount of restriction CR1, CR2, and CR3 is as follows:

$$CR1(=zero)<CR2<CR3.$$

FIG. 12D shows angles θ1, θ2, and θ3, which are formed between the straight line 93L connecting the cathode 91 and the anode 92 of the X-ray generator 13 serving as the X-ray generation source to each other, and the respective central axes L1, L2, and L3 of the X-ray beams BX1, BX2, and BX3 emitted from the X-ray generation part 10 in the respective imaging modes.

The central axes L1, L2, and L3 pass through central portions of the spreads having the radiation ranges SP1, SP2, and SP3, respectively, which are similar to the radiation range (spread) SP of the X-ray beam BX as viewed along the line-of-sight direction D of FIG. 1C.

It may be considered that the axial direction of each of the central axes L1, L2, and L3 is a line-of-sight direction when the target surface 94S is viewed in the direction opposite to the direction of radiation of the X-ray beam. The focal spot size varies among line-of-sight directions of the respective central axes L1, L2, and L3.

Firstly, as shown in FIG. 12A, when the large-FOV imaging mode is performed, the X-ray beam BX1 is emitted from the X-ray generation part to the whole of the relatively large imaging region R1. The X-ray beam BX1 is obtained as a result of the X-ray beam BX generated by the X-ray generator 13 being shaped by the beam passing hole 151. In the X-ray imaging apparatus 100, by revolving the revolving arm 30, the X-ray generation part 10 and the X-ray detection part 20 are rotated through 180 degrees or more around a central point C1 of the imaging region R1. In this manner, the X-ray beam BX1 is radiated to the imaging region R1 while rotating the X-ray generation part 10.

On the other hand, as shown in FIG. 12B, when the small/narrow-FOV imaging mode is performed, the X-ray beam BX2 is radiated from the X-ray generation part 10 to the whole of the relatively small imaging region R2. The radiation range of the X-ray beam BX2 is narrower than the X-ray beam BX1. This is realized by the blocking plate 171 blocking a part of the opening of the beam passing hole 151 of the beam-shaping plate 15.

Beam passing holes having a plurality of sizes may be provided in the beam-shaping plate 15 for the purpose of CT imaging, and the beam-shaping plate 15 may be moved to selectively bring the beam passing hole into a position before the X-ray passing hole 164 of the X-ray generator 13, though not shown.

The beam passing holes having the plurality of sizes may be beam passing holes of square shape having a plurality of sizes, for example.

A central point C2 of the imaging region R2 is positioned eccentrically with respect to the central point C1 of the imaging region R1. By controlling the X-axis motor 60X, the Y-axis motor 60Y, and the revolving motor 60R described above, the revolution shaft 31 and the revolving arm 30 are driven, and thus a drive control can be made to cause the X-ray generator 13 and the X-ray detector 21 to revolve around the central point C2.

Here, as described with reference to FIGS. 1A, 1B, 2A, and 2B, an apparent X-ray generation surface is smaller in an X-ray at the anode 92 side (−x side) than in an X-ray corresponding to the cathode 91 side (+x side) in the X-ray beam BX1. In this preferred embodiment, in order that such an X-ray corresponding to the portion having a small focal spot size can be used for the CT imaging, the blocking plate 171 blocks passing of the X-ray at the cathode 91 side, thus shaping the X-ray beam BX2.

The focal spot size (the apparent size of the X-ray generation surface when viewed along the central axis L2 of the X-ray beam BX2) of the X-ray beam BX2 thus shaped is smaller than not only the focal spot size (the apparent size of the X-ray generation surface when viewed along the central axis L1 of the X-ray beam BX1) of the X-ray beam BX1, but also the focal spot size obtained when the passing of the X-ray at the anode 92 side (−x side) is blocked.

As shown in FIG. 12D, the angle $\theta_2$ formed between the straight line 93L and the central axis L2 of the X-ray beam BX2 is larger than the angle $\theta_1$ formed between the straight line 93L and the central axis L1 of the X-ray beam BX1.

In this manner, when the imaging region is relatively narrow and the radiation range of the radiated X-ray beam BX2 is narrower than the X-ray beam BX1, the X-ray CT imaging is performed using an X-ray having a small focal spot size. This can suppress occurrence of blurring (so-called defocusing) in the X-ray image, and improve the image resolution.

As shown in FIG. 12C, when the panoramic imaging mode is performed, the very narrow X-ray beam BX3 is radiated from the X-ray generation part 10 to the imaging region R3. The imaging region R3 corresponds not to a CT imaging region but to the object M1 (for example, the head of a human body) including a panoramic imaging region. The X-ray beam BX3 is shaped by the beam passing hole 152 of the beam-shaping plate 15. Here, in the same manner as a case of the small-FOV imaging mode described above, the X-ray imaging apparatus 100 allows, in the X-ray beam BX1, only the X-ray at the anode 92 side which has a small focal spot size to pass through the beam passing hole 152.

The X-ray CT imaging in the large-FOV imaging mode may be performed with the entire area of a detection surface of the X-ray detector 21 whose detection surface is so large as to allow the whole head to be imaged, and the X-ray CT imaging in the small-FOV imaging mode may be performed with a partial area of the detection surface, and the panoramic imaging in the panoramic imaging mode may be performed with a further limited area of the detection surface. Alternatively, by using an X-ray detector such as the X-ray detector 21 shown in FIG. 9 having the detection element group 211 for X-ray CT imaging and the detection element group 212 for panoramic imaging which are separate from each other, the X-ray CT imaging in the large-FOV imaging mode may be performed with the entire area of the detection element group 211, and the X-ray CT imaging in the small-FOV imaging mode may be performed with a partial area of the detection element group 211, and the panoramic imaging in the panoramic imaging mode may be performed with the detection element group 212.

In a case where the X-ray detector 21 shown in FIG. 9 is used, the detector holder 22 is driven and controlled such that the detection element group irradiated with the X-ray beam is selected in accordance with the CT imaging and the panoramic imaging.

It may be also acceptable to independently provide a special detection surface corresponding to each imaging mode.

In a case where a common detection surface is shared by different modes, a signal transfer process can be efficiently performed by reading out only a region of the detection surface corresponding to an X-ray radiation range.

When the X-ray passes in the above-described manner, the focal spot size (the apparent size of the X-ray generation surface of the X-ray beam BX3 when viewed along the central axis L3 of the X-ray beam BX3) of the X-ray beam BX3 is smaller than the focal spot size of the X-ray beam BX1 or BX2. As shown in FIG. 12D, the angle $\theta_3$ formed between the straight line 93L and the central axis L3 of the X-ray beam BX3 is larger than the angles $\theta_1$ and $\theta_2$.

The angle formed between the straight line 93L and each of the central axes L1, L2, and L3 of the X-ray beams BX1, BX2, and BX3 is called a center-beam radiation angle, and the center-beam radiation angles $\theta_1$, $\theta_2$, and $\theta_3$ satisfy the following magnitude relation:

$$\theta_1 < \theta_2 < \theta_3.$$

Here, the angle formed between the straight line 93L and the central axis of the X-ray beam is increased in the imaging mode having a smaller or a narrower range of radiation of the X-ray beam.

The straight line 93L and the central axes L1, L2, and L3 are perpendicular to the revolution shaft 31, and set on the same plane.

It is necessary that the X-ray generator 13 and the X-ray detector 21 radiate the X-ray beam BX3 while moving on the panoramic-imaging orbit. By controlling the X-axis motor 60X, the Y-axis motor 60Y, and the revolving motor 60R described above, the revolution shaft 31 and the revolving arm 30 are driven, and the X-ray generator 13 and the X-ray detector 21 can be driven and controlled so as to move on the panoramic-imaging orbit.

Here, although a description partly overlaps the above description regarding the configuration of revolving the X-ray generation part 10 and the X-ray detection part 20 relative to the object M1 in a case of the X-ray CT imaging, a control of movement of the X-ray generation part 10 and the X-ray detection part 20 will be mentioned.

The revolution shaft 31 can be controlled by the X-table 35X and the Y-table 35Y so as to move two-dimensionally. Thus, the X-ray generation part 10 and the X-ray detection part 20 can be moved by a combined motion in which the two-dimensional movement of the revolution shaft 31 caused by the X-table 35X and the Y-table 35Y, and the revolution of the revolving arm 30 around the revolution shaft 31 can be simultaneously performed.

The X-ray generation part 10 and the X-ray detection part 20 may be revolved on a the true-circle orbit around a rotation shaft set in a position different from the position of the revolution shaft 31, or may be moved and revolved on an orbit not having a true-circle shape.

It may be acceptable that: the two-dimensional movement of the revolution shaft 31 is stopped, and only the revolving motion of the revolving arm 30 around the revolution shaft 31 is performed; and the X-ray generation part 10 and the X-ray detection part 20 are revolved with the center of the revolution of the X-ray generation part 10 and the X-ray detection part 20 being placed at the same position as that of the axis of the revolution shaft 31. It may be also acceptable that the revolving motion of the revolving arm 30 around the revolution shaft 31 is stopped, and only the two-dimensional movement of the revolution shaft 31 is performed, to thereby move the X-ray generation part 10 and the X-ray detection part 20 in parallel with each other in the same direction.

This movement control allows a correction of the orbit of the movement of the conventional revolving arm 30 or the movement the conventional X-ray generation part 10 and X-ray detection part 20 in the panoramic imaging. The combined motion in which the two-dimensional movement of the revolution shaft 31 caused by the X-table 35X and the Y-table 35Y and the revolution of the revolving arm 30 around the revolution shaft 31 are simultaneously performed allows such a control that the X-ray beam BX3 obliquely incident on the X-ray detection part 20 as shown in FIG. 12C can follow the same trajectory as the movement trajectory formed by the movement of the conventional revolving arm 30 or the movement of the conventional X-ray generation part 10 and X-ray detection part 20.

Thus, in this preferred embodiment, the panoramic imaging is performed by using the X-ray beam BX3 whose focal spot size viewed along the central axis direction of the X-ray beam is smaller than in a case of the X-ray CT imaging. Thereby, generation of blurring in the X-ray image is reduced, to improve the image resolution.

The beam shaping mechanism 16 for changing the focal spot size is driven and controlled by the X-ray generation part control section 601a. The CPU 601 functions as an emission control section configured mainly of the X-ray generation part control section 601a. The X-ray generation part control section 601a itself may be considered as the emission control section.

In this preferred embodiment, the configuration of moving the beam passing hole of the beam-shaping plate 15 relative to the X-ray generator 13 which does not move within the X-ray generation part 10 is described. However, it may be also acceptable that a movement mechanism (not shown) of the X-ray generator 13 is provided, and the X-ray generator 13 is moved (for example, the X-ray generator 13 is moved in the X-axis direction) relative to the beam passing hole of the beam-shaping plate 15 which does not move within the X-ray generation part 10, so that the movement of the beam passing hole of the beam-shaping plate 15 relative to the above-described X-ray generator 13 can be realized in a relative manner. This is an example of a configuration for changing the focal spot size of an X-ray beam by displacing an X-ray tube within an X-ray generator 13. In this case, the beam-shaping plate 15 may switch only the opening degree of the beam passing hole in accordance with each imaging mode, in the same manner as described above.

In this preferred embodiment, the CT imaging is performed with the large-radiation-field X-ray CT imaging mode and the small-radiation-field X-ray CT imaging mode. In both of the radiation fields, the revolution of the revolving arm 30 may be stopped to perform a simple perspective imaging.

As already described, in the X-ray imaging apparatus 100, similarly to the X-ray CT imaging apparatus disclosed in Japanese Patent Application Laid-Open No. 2007-29168, the rotation axis of the X-ray generation part 10 and the X-ray detection part 20 can be set at a position different from the position of the mechanical revolution shaft 31. The X-ray imaging apparatus 100 rotates the X-ray generation part 10 and the X-ray detection part 20 around a particular rotation axis which is set in a position different from the position of the revolution shaft 31, by the combined motion of the movement of the revolving arm 30 in the horizontal plane caused by the movement of the revolution shaft 31 and the revolution of the revolving arm 30 around the revolution shaft 31. In this respect, a specific description will be given with reference to FIGS. 12E to 12H. In FIGS. 12E to 12H, the object M1 indicates a human head, and a dental arch S is shown.

The spread angle, as viewed along the line-of-sight direction D, of each of the radiation range SP1 in the large-radiation-field X-ray CT imaging mode (that is, a wide-radiation-field X-ray CT imaging mode, the large-FOV imaging mode, the wide-FOV imaging mode), the radiation range SP2 in the small-radiation-field X-ray CT imaging mode, (that is, a narrow-radiation-field X-ray CT imaging mode, the small-FOV imaging mode, the narrow-FOV imaging mode), and the radiation range SP3 in the panoramic imaging mode can be arbitrarily set. The size of the imaging region R1 in the large-FOV imaging mode, the size of the imaging region R2 in the small-FOV imaging mode, and the like, can be arbitrarily set. An example thereof is as follows.

By utilizing the placement of the X-ray generation part 10 and the X-ray detection part 20, the determination of the length of the revolution arm 30, and the like, the distance between the target surface 94S and the X-ray detector 21 is set to approximately 500 to 550 mm, and preferably to exactly or approximately 515 mm. This range is conventionally considered to be suitable for panoramic imaging.

An example in a case of the large-radiation-field X-ray CT imaging mode is as follows.

The diameter of the imaging region R1 is set to 70 to 100 mm, and preferably to exactly or approximately 80 mm.

The spread angle of the radiation range SP1 is set to 11 to 16.5 degrees, and preferably to exactly or approximately 13 degrees.

The width of the X-ray beam BX1 in the X-ray detection surface of the X-ray detector 21 is set to 103 to 150 mm, and preferably to exactly or approximately 120 mm.

This is a range covering the whole range or substantially the whole range of a dental arch, and corresponds to the X-ray detection surface of the X-ray detector of relatively low price.

An example in a case of the small-radiation-field X-ray CT imaging mode is as follows.

The diameter of the imaging region R2 is set to 15 to 50 mm, and preferably to exactly or approximately 40 mm.

The spread angle of the radiation range SP2 is set to 3 to 8 degrees, and preferably to exactly or approximately 7 degrees.

The width of the X-ray beam BX2 in the X-ray detection surface of the X-ray detector 21 is set to 25 to 83 mm, and preferably to exactly or approximately 67 mm.

This is a range covering one to five teeth, and in a preferred embodiment, three or four teeth. This allows a partial CT imaging using a small dosage of X-ray in a case where observation of only a part of the teeth suffices.

An example in a case of the panoramic imaging mode is as follows.

The spread angle of the radiation range SP3 is set to 0.45 to 0.67 degrees, and preferably to exactly or approximately 0.51 degrees.

The width of the X-ray beam BX3 in the X-ray detection surface of the X-ray detector 21 is set to 4 to 6 mm, and preferably to exactly or approximately 4.6 mm. The width of the X-ray beam BX3 in a region where the X-ray beam passes through the tooth or teeth varies depending on a scanned region, and approximately 3 to 4 mm, which enables sharp panoramic imaging.

Needless to say, the above-mentioned embodiment is merely an example. Thus, for example, the diameter of the imaging region R1 in the large-radiation-field X-ray CT imaging mode (the large-FOV imaging mode) may be set to exactly or approximately 170 mm so as to cover the whole range or substantially the whole range of the head of a human being.

FIGS. 12E and 12F show an example of driving of the revolving arm 30 shown in FIG. 12A. FIG. 12F shows a situation where the revolving arm 30 is, from a state shown in FIG. 12E, revolved in the clockwise direction through 90 degrees in a plan view, so that the revolution shaft 31 (revolution shaft center 31c) is revolved (turned) through 90 degrees around the central point C1 serving as the revolution center.

The revolving arm 30 is structured so as to be revolved around the revolution shaft 31 (strictly, the revolution shaft center 31c of the revolution shaft 31), and the revolution shaft 31 is structured so as to be revolved (turned) around the central point C1 of the imaging region R1 serving as the revolution center by the two-dimensional movement mechanism 35M. By the angle of revolution of the revolving arm 30 around the revolution shaft 31 (revolution shaft center 31c), the revolution shaft 31 (revolution shaft center 31c) is revolved (turned) in the same direction around the central point C1 serving as the revolution center, as indicated by the arrow, to move from a position PL1 to a position PL2. At this time, the revolution shaft 31 moves in a circular arc having radius r1. This revolution of the revolving arm 30 is performed through a revolution angle necessary for the CT imaging. This drive control enables the X-ray generation part 10 and the X-ray detection part 20 to be rotated around the central point C1 serving as the rotation center (that is, the rotation axis) which is set in a position different from the position of the revolution shaft 31 (revolution shaft center 31c).

FIGS. 12G and 12H show an example of driving of the revolving arm 30 shown in FIG. 12B. FIG. 12H shows a situation where the revolving arm 30 is, from a state shown in FIG. 12G, revolved in the clockwise direction through 90 degrees in a plan view, so that the revolution shaft 31 (revolution shaft center 31c) is revolved (turned) through 90 degrees around the central point C1 serving as the revolution center.

In the X-ray imaging shown in FIGS. 12G and 12H, the positions of the imaging region R2 and the central point C2 are different from the positions of the imaging region R1 and the central point C1, respectively. The revolution shaft 31 (revolution shaft center 31c) does not move from the position PL1 to the position PL2, but moves from a position PL21 to a position PL22 around the central point C2 so as to make a circular arc having radius r2. This drive control enables the X-ray generation part 10 and the X-ray detection part 20 to be rotated around the central point C2 serving as the rotation center (that is, the rotation axis) which is set in a position different from the position of the revolution shaft 31 (revolution shaft center 31c).

In the X-ray imaging shown in FIGS. 12E and 12F, the imaging region R1 includes the entire region of the dental arch including a jaw bone. In the X-ray imaging shown in FIGS. 12G and 12H, the imaging region R2 includes a part of the dental arch. Using either one of the entire region and a partial region of the dental arch as an imaging region as shown in FIGS. 12E to 12H allows a whole observation and a partial observation of the dental arch, respectively. Needless to say, the size of the imaging region is not limited to the ones shown in FIGS. 12E to 12H. The size of the imaging region is set depending on the size of a detection surface area of the X-ray detector 21, or the like.

The movement of the revolving arm 30 described above is a movement relative to the object (or the imaging region). Thus, the motion of the revolution shaft 31 relative to the central points C1, C2 may be partially or entirely replaced with the motion of the object. For example, an object two-dimensional movement mechanism (not shown) may be provided for two-dimensionally moving the object holding part 421 in the aforementioned two-dimensional plane defined by the X-axis direction and the Y-axis direction. The object M1 is moved by the object two-dimensional movement mechanism, and thereby the central point C1 can be moved.

FIG. 12I is a diagram showing panoramic imaging performed by the combined motion of the movement of the revolving arm 30 in the horizontal plane caused by the movement of the revolution shaft 31 and the revolution of the revolving arm 30 around the revolution shaft 31. In this panoramic imaging, the X-ray generator 13 and the X-ray detector 21 (strictly, the detection surface of the X-ray detector 21) are revolved with the dental arch S interposed therebetween, and for example, the X-ray beam BX3 moves from a position for radiating an X-ray to a left jaw to a position for radiating an X-ray to the right jaw through the middle of front teeth. That is, the X-ray generator 13 moves in the order of positions Lt1, Lt2, Lt3, and Lt4, and moves to a position Lt5. On the other hand, the X-ray detector 21 moves in the order of positions Lr1, Lr2, Lr3, and Lr4, and moves to a position Lr5. A curved line La in FIG. 12I indicates an envelope curve drawn by a trajectory of the X-ray beam BX3. In the panoramic imaging, it is preferable to control the revolving movement of the revolving arm 30 such that the X-ray beam BX3 can form this envelope curve.

The revolving arm 30 is pivoted on the mechanical revolution shaft 31, but the positional relationship between the revolving arm 30 and the revolution shaft 31 is fixed and they are not displaced relative to each other. On the other hand, among different imaging types such as the panoramic imaging and the CT imaging, the revolving arm 30 moves different orbits. Thus, it is necessary to set an orbit adapted to an imaging type. In this preferred embodiment, the revolving arm 30 can be moved on an orbit adapted to each imaging type, by the combined motion of the movement of the revolving arm 30 in the horizontal plane caused by the movement of the revolution shaft 31 of the two-dimensional movement mechanism 35M and the revolution of the revolving arm 30 around the revolution shaft 31.

Simply revolving the revolving arm 30 around the revolution shaft 31 allows the CT imaging to be performed for an imaging region having merely a certain largeness. However, as described above, by moving the revolution shaft 31 of the two-dimensional movement mechanism 35M to thereby move the revolving arm 30 in the horizontal plane, the CT imaging for imaging regions having different largenesses can be performed by using the same revolving arm 30.

When the X-ray generator 13 is not rotated relative to the X-ray detection part 10 as shown in FIGS. 12A to 12I, the X-ray beams BX2 and BX3 in the X-ray beam BX1 which are deviated to the side having a smaller focal spot size are radiated to the object M1 as shown in FIGS. 12B and 12C. In this case, a drive control in which the movement of the revolving arm 30 in the horizontal plane caused by the movement of the revolution shaft 31 of the two-dimensional movement mechanism 35M is combined with the revolution of the revolving arm 30 around the revolution shaft 31 is particularly effective.

2. Second Preferred Embodiment

In the above-described preferred embodiment, as shown in FIGS. 12A to 12D, in order that the X-ray emitted from a portion having a small focal spot size can be radiated to the imaging region, the X-ray beams BX2 and BX3 at the anode 92 side in the X-ray beam BX1 are radiated to the imaging regions R2 and R3. Therefore, the X-ray detection part 20 detects the X-ray at a position deviated toward the anode 92 side. However, the position at which the X-ray is detected is not limited thereto. This preferred embodiment shows an example of a configuration of changing the focal spot size of the X-ray beam by displacing the X-ray tube within the X-ray generator 13A. In the following description, elements having the same functions as those of the first preferred embodiment are appropriately denoted by the same corresponding reference numerals, without descriptions thereof.

FIG. 13 is a perspective view showing an X-ray generator 13A according to a second preferred embodiment. As shown in FIG. 13, the X-ray generation part 10 according to this preferred embodiment includes a rotating motor 96 which rotates the X-ray generator 13A around a rotation shaft 95 extending in the vertical direction in the X-ray generator 13A. The rotating motor 96 is fixed to the motor fixing plate 10A, and an operation thereof is controlled by the X-ray generation part control section 601a. In an illustrated example, the motor fixing plate 10A is fixed to the X-ray generation part 10 within the X-ray generation part 10.

The CPU 601 functions as an emission control section configured mainly of the X-ray generation part control section 601a. The X-ray generation part control section 601a itself may be considered as the emission control section. The X-ray generator 13A rotates (turns) around the rotation shaft 95, thereby rotating relative to the X-ray generation part 10. An axial direction of the axis (rotation axis) AC1 of the rotation shaft 95 can be defined as, for example, a direction parallel to the axial direction of the revolution shaft 31.

The embodiment shown in FIG. 13, the X-ray tube 9 rotates integrally with the X-ray generator 13A in which the X-ray tube 9 is accommodated.

The axial direction of the axis (rotation axis) AC1 of the rotation shaft 95 can also by defined as the same direction as the line-of-sight direction D described with reference to FIG. 1. The displacement of the X-ray generation source 13A is controlled by driving the rotating motor 96 to thereby control a change of the angle of rotation of the X-ray generator 13A relative to the X-ray generation part 10.

Figure 14A:
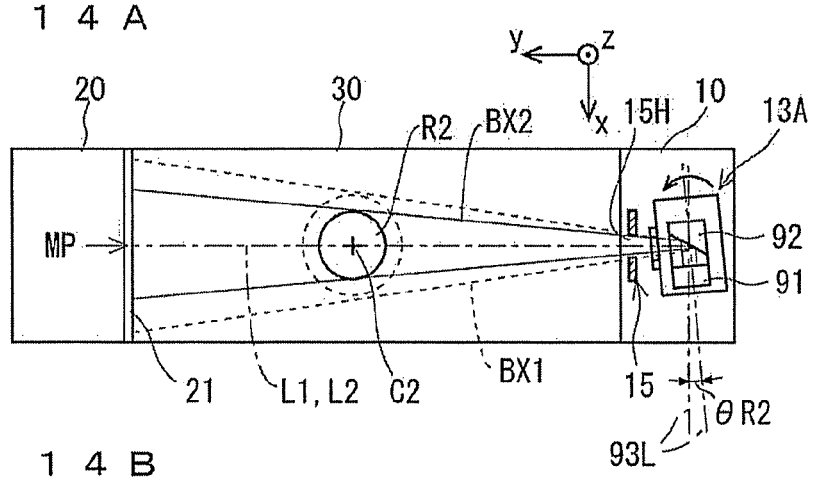
FIGS. 14A and 14B are schematic top views of the X-ray imaging apparatus, showing a situation where X-ray imaging is performed.
Figure 14B:
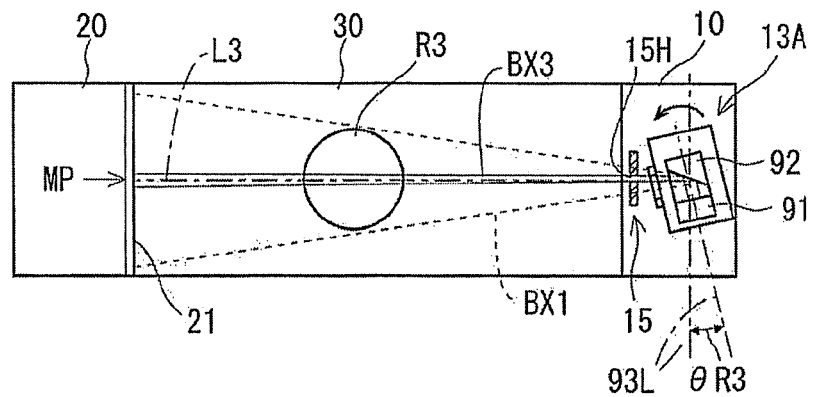

FIGS. 14A and 14B are schematic top views of the X-ray imaging apparatus 100 showing a situation where the X-ray imaging is performed. FIG. 14A shows a situation where the small-FOV imaging mode for the CT imaging of a relatively small region is performed. FIG. 14B shows a situation where the panoramic imaging mode is performed. A situation where the large-FOV imaging mode for the CT imaging of a relatively large region is the same as shown in FIG. 12A, and therefore not shown.

In this preferred embodiment, in a case where the small-FOV imaging mode is performed, as shown in FIG. 14A, the X-ray beam BX2 is emitted in a state where the X-ray generator 13A is rotated through a predetermined angle around the rotation shaft 95 shown in FIG. 13. At this time, by controlling the beam shaping mechanism 16, the opening of the beam passing hole 151 shown in FIG. 7 is blocked by the blocking plate 171 shown in FIG. 7, thus shaping the X-ray beam BX2.

In a case where the panoramic imaging mode is performed, as shown in FIG. 14B, the X-ray generator 13A is further rotated as compared with the small-FOV imaging mode, to radiate the narrow X-ray beam BX3 to the imaging region R3. The X-ray beam BX3 is shaped by the beam passing hole 153 shown in FIG. 7. The imaging region R3 corresponds not to a CT imaging region but to the object M1 (for example, the head of a human body) including a panoramic imaging region.

When the position of the X-ray tube 9 shown in FIG. 12A is defined as a reference rotation position, it can be recognized by the angle through which the X-ray tube 9 is rotated relative to the reference rotation position in each mode.

The angle of rotation of the straight line 93L shown in FIG. 12A relative to the straight line 93L shown in FIG. 12A is defined as $\theta R1$ (=zero). The angle of rotation of the straight line 93L shown in FIG. 14A relative to the straight line 93L shown in FIG. 12A is defined as $\theta R2$. The amount of rotation of the straight line 93L shown in FIG. 14B relative to the straight line 93L shown in FIG. 12A is defined as $\theta R3$. Thus, these three values satisfies satisfy the following relationship:

$$\theta R1 (=\text{zero}) < \theta R2 < \theta R3.$$

Here, the X-ray generator 13A is set so as to be displaced in such a manner that the angle formed between the straight line 93L and the central axis of the X-ray beam is increased in an imaging mode having a smaller range of radiation of the X-ray beam.

The magnitude relation among the center-beam radiation angle $\theta 1$ formed between the straight line 93L and the central axis L1 of the X-ray beam BX1 in the large-FOV imaging mode of FIG. 12A, the center-beam radiation angle $\theta 2$ formed between the straight line 93L and the central axis L2 of the X-ray beam BX2 in the small-FOV imaging mode of FIG. 14A, the center-beam radiation angle θ3 formed between the straight line 93L and the central axis L3 of the X-ray beam BX3 in the panoramic imaging mode of FIG. 14B, is the same as shown in FIG. 12D, and therefore an illustration and a description thereof are omitted.

How the detection surface is used in each mode is the same as shown in FIGS. 12A to 12D, and therefore a specific description thereof is omitted. The magnitude relation or the largeness relation among the radiation ranges and the opening widths of the opening portion 15H in the large-FOV imaging mode, the small-FOV imaging mode, and the panoramic imaging mode is the same as the case of FIGS. 12A to 12D. Also, the amount of restriction of the emission range in a portion of the X-ray beam closer to the cathode 91 in the radiation range having the spread SP of FIG. 1A is the same as the case of FIGS. 12A to 12D. Thus, detailed descriptions thereof will be omitted.

In FIGS. 14A and 14B as well, the straight line 93L and the central axes L1, L2, and L3 are perpendicular to the revolution shaft 31, and set in the same plane.

As described above, the X-ray beams BX2 and BX3 are emitted in a state where the X-ray generator 13A is rotated relative to the X-ray detection part 20, thereby making the X-ray incident on a middle portion MP of the X-ray detection part 20. Radiating the X-ray in this manner enables a detection of the middle portion MP of the X-ray detection part 20. For example, in a case where the detection surface for panoramic imaging is provided at the middle portion MP, this configuration enables an effective detection of an X-ray.

3. Third Preferred Embodiment

In the first preferred embodiment, as shown in FIG. 12C, when the panoramic imaging mode is performed, the X-ray beam BX3 is obliquely incident on the X-ray detector 21. Here, it may be acceptable to make the X-ray beam BX3 incident on the X-ray detector 21 in a direction substantially perpendicular thereto by rotating the detector 21.

Figure 15:
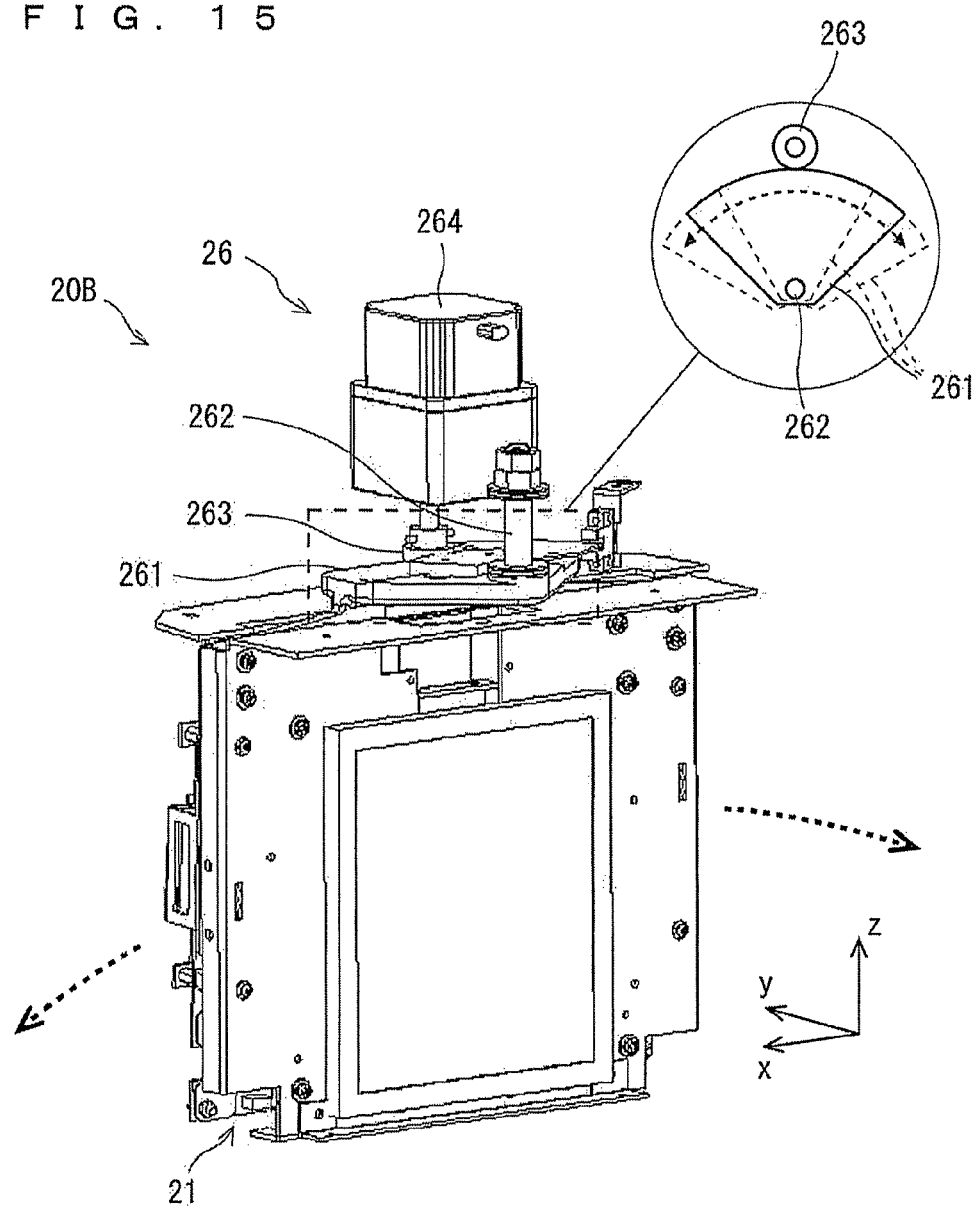
FIG. 15 is a perspective view showing an X-ray detection part according to a third preferred embodiment.

FIG. 15 is a perspective view showing an X-ray detection part 20B according to a third preferred embodiment. The X-ray detection part 20B includes a turning mechanism 26 for turning the X-ray detector 21. The turning mechanism 26 includes a fan-shaped member 261 having an arcuate end portion, and a switching shaft 262 extending in the vertical direction. The turning mechanism 26 further includes a rotating member 263 which rotates in contact with the arcuate end portion of the fan-shaped member 261, and a rotation drive motor 264 which moves the rotating member 263 in rotation.

The switching shaft 262 and the rotation drive motor 264 are fixed in a certain position within the X-ray detection part 20, though not shown. The switching shaft 262 turnably supports an axis of the fan-shaped member 261. Based on a control signal supplied from the X-ray detection part control section 601b, the rotation drive motor 264 rotates the rotating member 263 which is in contact with the arcuate end portion of the fan-shaped member 261, thereby turning the fan-shaped member 261 around the switching shaft 262. The X-ray detector 21 is fixed to the fan-shaped member 261, and turns together with the fan-shaped member 261.

By the turning mechanism 26 turning the fan-shaped member 261 around the switching shaft 262 extending in parallel with the revolution shaft 31, the X-ray detector 21 is turned within a predetermined range (for example, a range in which the angle of rotation around the switching shaft 262 is 90 degrees or less).

The above-described configuration enables the orientation of the detection surface of the X-ray detector 21 to be adjusted to some extent. The turning mechanism 26 is an example of means for turning the X-ray detector 21, and should not be construed as being limitative.

Figure 16:
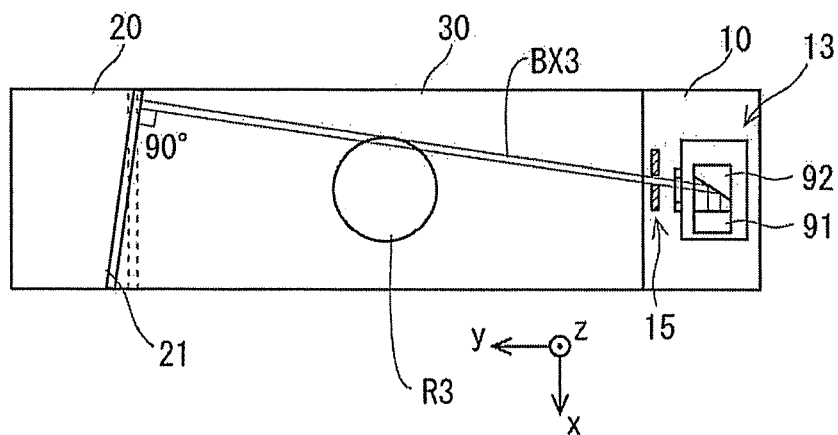
FIG. 16 is a diagram schematically showing a panoramic imaging mode using the X-ray detection part.

FIG. 16 is a diagram schematically showing the panoramic imaging mode using the X-ray detection part 20B. In this preferred embodiment, as shown in FIG. 16, during the panoramic imaging, the turning mechanism 26 brings the X-ray detector 21 into a position which is turned through a predetermined angle toward the anode 92 side, thereby making the X-ray beam BX3 incident on the X-ray detector 21 in a direction substantially perpendicular thereto. Thus, an X-ray incident on the X-ray detector 21 substantially perpendicularly thereto can be detected, and therefore the panoramic imaging using an X-ray having a small focal spot size can be performed in an effective manner.

4. Fourth Preferred Embodiment

In the first preferred embodiment, in the panoramic imaging mode or the like, the X-ray beam is detected at a position of the X-ray detection part 20 deviated toward the anode 92 side, as shown in FIG. 12C. For example, in a case where the detection surface for panoramic imaging is set at a portion other than an end portion of the X-ray detector 21, the X-ray beam transmitted through the imaging region R3 may not be effectively detected. Therefore, in this preferred embodiment, this problem is solved by moving the X-ray detector 21.

Figure 17:
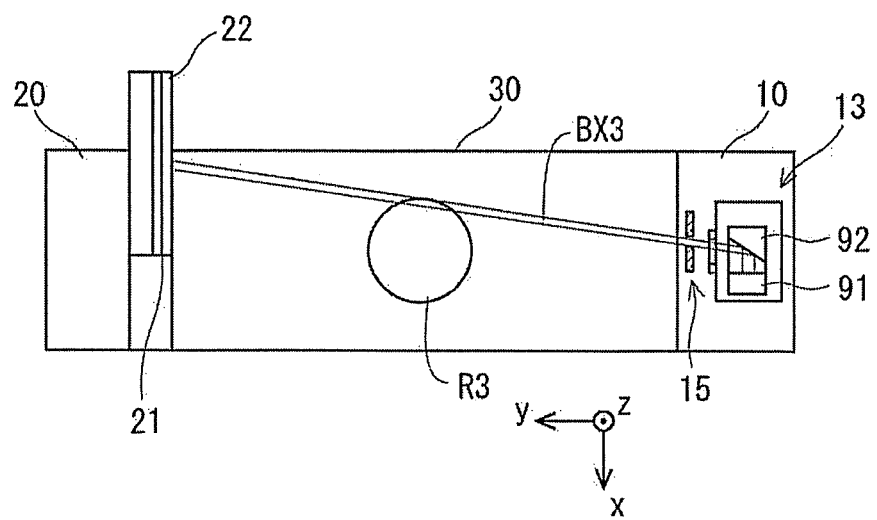
FIG. 17 is a schematic top view showing a situation where panoramic imaging is performed in an X-ray imaging apparatus according to a fourth preferred embodiment.

FIG. 17 is a schematic top view showing a situation where the panoramic imaging is performed in an X-ray imaging apparatus 100 according to a fourth preferred embodiment. As shown in FIG. 17, in this preferred embodiment, the movement motor 24 is driven to move the detector holder 22 along the guide rail 23 (see FIG. 8), to thereby making an X-ray received at a middle portion of the X-ray detector 21. In this manner, even when the X-ray detection surface is not provided at the end portion, an effective detection of the X-ray beam is allowed by moving the X-ray detector 21.

It may be also acceptable that the guide rail 23 is formed in an arch-like shape so that the X-ray detector 21 is moved in an arc around a focal point of the X-ray beam of the X-ray generator 13, though not shown. Thereby, during the panoramic imaging, the X-ray detector 21 can be placed in a position turned through a predetermined angle toward the anode 92 side, and the X-ray beam BX3 can be made incident on the X-ray detector 21 substantially perpendicularly thereto.

5. Fifth Preferred Embodiment

In the configuration of the above-described preferred embodiment, the target surface 94S of the anode 92 of the X-ray generator 13 is arranged so as to be parallel to the vertical direction and inclined relative to the Y-axis direction, thus performing the X-ray CT imaging mode. However, a manner of arrangement of the target surface is not limited thereto.

Figure 18A:
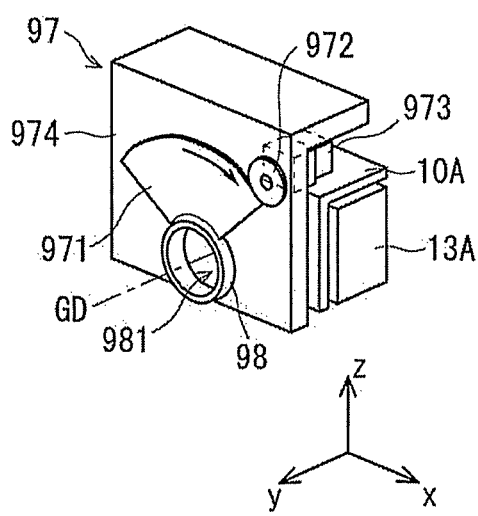
FIGS. 18A, 18B, 18C, and 18D are perspective views schematically showing an X-ray generator and a turnover mechanism included in an X-ray generation part according to a fifth preferred embodiment.
Figure 18B:
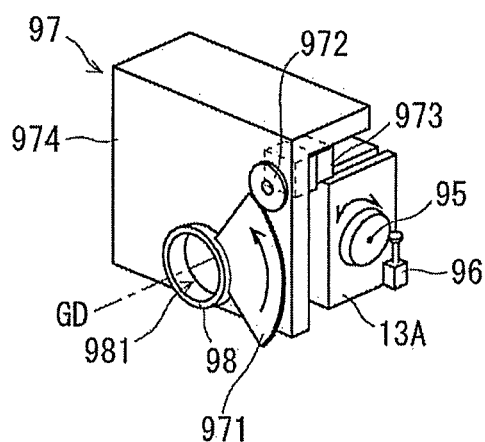
Figure 18C:
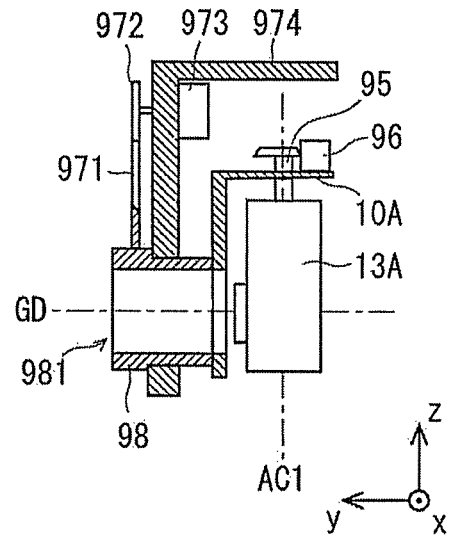
Figure 18D:
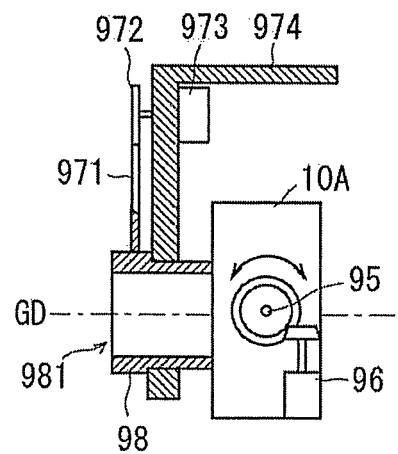

FIGS. 18A to 18D are perspective views schematically showing an X-ray generator 13A and a turnover mechanism 97 included in an X-ray generation part 10 according to a fifth preferred embodiment. FIGS. 18A and 18B are perspective views obtained when the turnover mechanism 97 is obliquely seen. FIGS. 18C and 18D are side views obtained when the X-ray generator 13A shown in FIGS. 18A and 18B is seen along the x direction from the lateral side, respectively.

The X-ray generation part 10 of this preferred embodiment includes the X-ray generator 13A described in the second preferred embodiment and the turnover mechanism 97. The turnover mechanism 97 turns the X-ray generator 13A through 90 degrees around a straight line connecting the X-ray generation part 10 to the X-ray detection part 20, for example, around a straight line GD connecting a middle portion of the X-ray detection surface to the center of the X-ray beam emitted from the X-ray generator 13A or a middle portion of the target surface 94S of the X-ray tube 9.

FIGS. 18B and 18D show state where the X-ray generator 13A shown in FIGS. 18A and 18C is turned through 90 degrees around the central axis of radiation of the X-ray beam, respectively. The angle of the turning may not be exactly 90 degrees, as long as the focal spot size can be effectively changed. Thus, it suffices that the angle of the turning is close to 90 degrees to such an extent that this purpose can be attained.

In the X-ray imaging apparatus 100 shown in FIG. 3, the X-ray detection part 20 is arranged at the slightly higher than the position of the X-ray generation part 10 in the axial direction of the revolution shaft 31. Accordingly, the straight line GD is set so as to be oriented toward the middle portion of the X-ray detection surface of the X-ray detector 21 arranged at a position slightly higher than the X-ray generator 13A.

The turnover mechanism 97 includes a fan-shaped member 971, a rotating member 972, a turnover motor 973, and a holding member 974. The fan-shaped member 971 is in the shape of a flat plate having an arcuate end portion. The rotating member 972 rotates along the arcuate end portion of the fan-shaped member 971. The turnover motor 973 rotates the rotating member 972. The holding member 974 integrally holds the fan-shaped member 971, the rotating member 972, and the turnover motor 973.

The fan-shaped member 971 has a cylindrical link portion 98 extending horizontally. The link portion 98 is rotatably connected to the holding member 974. Through the link portion 98, the fan-shaped member 971 is coupled to the motor fixing plate 10A which turnably supports the X-ray generator 13A and is similar to that shown in FIG. 13.

An X-ray passing hole 981 which allows an X-ray beam to pass therethrough is formed at the center of the link portion 98. The X-ray beam emitted from the X-ray generator 13A can pass through the X-ray passing hole 981.

The motor fixing plate 10A shown in FIG. 18A has a wall portion extending to the front surface of the X-ray generator 13A to be coupled with the link portion 98. In the wall portion, a hole communicating with the X-ray passing hole 981 and allowing the X-ray beam emitted from the X-ray generator 13A to pass therethrough is provided.

The configuration of driving the X-ray generator 13A by the rotating motor 96 to turn around the rotation shaft 95 is the same as the case shown in FIG. 13, and therefore details thereof are not described here. In an example illustrated in FIGS. 18A to 18D, a driving mechanism of the motor 96 is driven by engagement between pinion gears or by slidable engagement between pinion-shaped rollers.

The rotating member 972 is coupled to the turnover motor 973 through, for example, a screw shaft of a ball screw (not shown). The turnover motor 973 is driven based on a control signal supplied from the X-ray generation part control section 601a. When the turnover motor 973 is driven, the rotating member 972 is rotated to rotate the fan-shaped member 971 around the link portion 98. This rotation of the fan-shaped member 971 rotates the X-ray generator 13A together with the motor fixing plate 10A through 90 degrees around the link portion 98 (FIG. 18B). The above-described configuration of the turnover mechanism 97 is merely an example, and a configuration of turning the X-ray generator 13A is not limited thereto.

The reference character AC1 in the drawing denotes a rotation axis of the turning of the X-ray generator 13A around the rotation shaft 95, and the position of the rotation axis is coincident with the position of the rotation shaft 95. This rotation axis AC1 is the same as that shown in FIG. 13. The reference character AC2 denotes a rotation axis of the link portion 98, which is a straight line connecting the X-ray generation part 10 and the X-ray detection part 20 to each other.

Figure 19A:
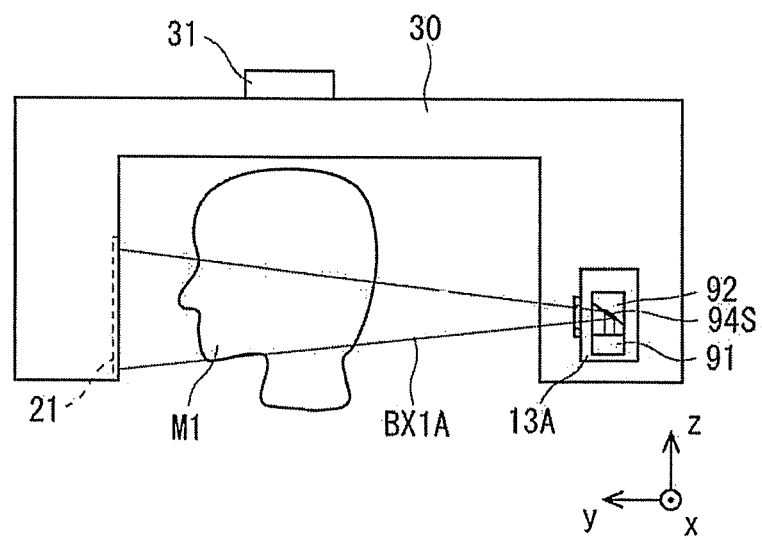
FIGS. 19A and 19B are schematic side views showing a situation where the X-ray imaging apparatus performs an X-ray CT imaging mode.
Figure 19B:
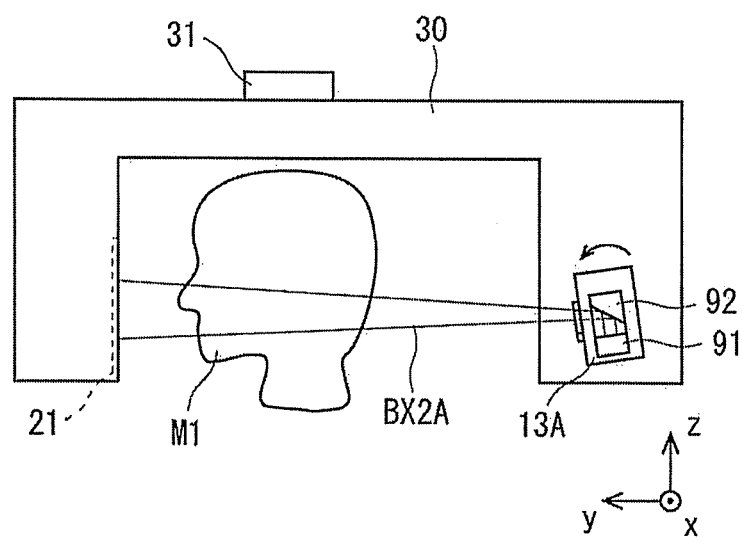

FIGS. 19A and 19B are schematic side views showing a situation where the X-ray imaging apparatus 100 performs the X-ray CT imaging mode. FIG. 19A shows a situation where the large/wide-FOV imaging mode for the CT imaging of a relatively large region is performed. FIG. 19B shows a situation where the small/narrow-FOV imaging mode for the CT imaging of a relatively small region is performed.

In this preferred embodiment, in a case where the panoramic imaging mode is selected, similarly to the above-described preferred embodiments (for example, in the first preferred embodiment), the X-ray imaging is performed while the X-ray generator 13A takes the posture as shown in FIG. 18A without being turned. The X-ray generator 13A is turned by driving of the rotating motor 96, and radiates an X-ray beam at an angle as shown in FIG. 14B.

On the other hand, in a case where the X-ray CT imaging mode is selected, the X-ray generation part control section 601a drives the turnover motor 973, thereby turning the X-ray generator 13A through 90 degrees.

When the X-ray generator 13A is turned, as shown in FIG. 19A, an electron beam is emitted from the cathode 91 at the lower side (−Z side) toward the anode 92 at the upper side (+Z side). The target surface 94S of the anode 92 is configured as a surface extending in parallel with the X direction and inclined toward the Y direction relative to the vertical direction (Z-axis direction). An X-ray beam generated by such a target surface 94S is emitted toward the X-ray detector 21.

Here, in an X-ray beam BX1A emitted from the turned X-ray generation part 13A, a portion at the anode 92 side (here, the +Z side) has a smaller apparent size (focal spot size) of the X-ray generation surface than a portion at the cathode 91 side (here, the −Z side). That is, by using the X-ray beam at the anode 92 side (+Z side) for imaging, the resolution of an X-ray image can be improved.

In this preferred embodiment, therefore, in a case where the small/narrow-FOV imaging mode for CT imaging of a relatively small region is performed in the X-ray CT imaging mode, as shown in FIG. 19B, the rotating motor 96 is driven to rotate the X-ray generator 13A around the X-axis and thus incline the X-ray generator 13A, so that, in the X-ray beam BX1A, an X-ray beam BX2A at the anode 92 side which has a smaller focal spot size is radiated to an imaging region.

In a case of the X-ray CT imaging mode, as compared with a case of the panoramic imaging, a range to which the X-ray beam is radiated is relatively larger in the horizontal direction. For example, in the X-ray beam BX1 shown in FIG. 12A, when the X-ray generation surface (target surface 94S) is seen from each point on the X-ray detector 21, the apparent size (focal spot size) varies with respect to the horizontal direction. In more detail, the focal spot size becomes smaller at a position closer to the +X side. In other words, the frequency of occurrence of blurring in an X-ray image increases at the −X side.

On the other hand, in this preferred embodiment, the X-ray generator 13A is turned through 90 degrees, and thereby such a variation in the focal spot size can be caused to occur in the vertical direction. When the X-ray generation surface is seen from each point on the X-ray detector 21, the apparent size (focal spot size) thereof is constant with respect to any point on the horizontal direction. Therefore, the X-ray beam BX1A whose resolving power is uniform in the horizontal direction can be generated.

In the panoramic imaging such as imaging of a dental arch, in general, the imaging is performed by using the X-ray beam BX3 having a cross-sectional surface elongated in the vertical direction. Therefore, in this case, it is preferable that apparent sizes of the X-ray generation surface seen from a plurality of points positioned along the vertical direction at the X-ray detector 21 side are identical. Thus, in the panoramic imaging mode, it is preferable that the X-ray generator 21 is not turned. In this manner, in this preferred embodiment, a direction in which the focal spot size is influenced can be controlled by turning the X-ray generator 13A. Therefore, imaging can be performed by using an X-ray beam suitable for each imaging mode.

6. Sixth Preferred Embodiment

The X-ray imaging apparatus 100 is also applicable to offset-scanning X-ray CT imaging.

Figure 20A:
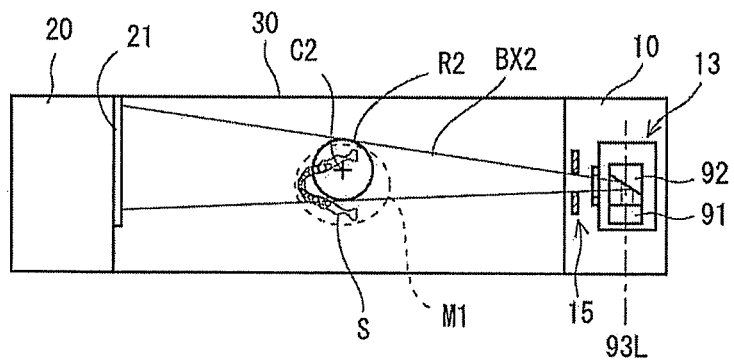
FIGS. 20A, 20B, and 20C are diagrams for explaining offset-scanning X-ray CT imaging.
Figure 20B:
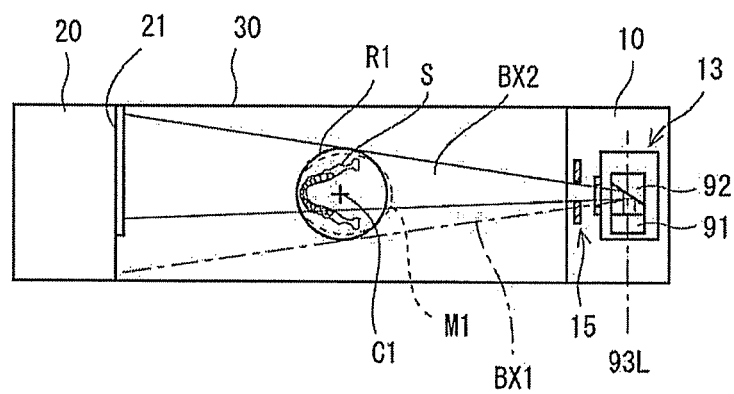
Figure 20C:
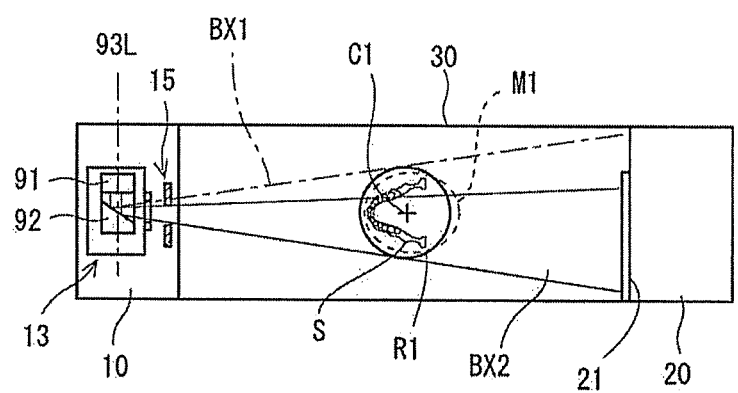

FIGS. 20A, 20B, and 20C are diagrams for explaining the offset-scanning X-ray CT imaging. FIG. 20A shows a schematic top view of the X-ray imaging apparatus 100 under the same X-ray radiation state as shown in FIG. 12B. However, the X-ray detector 21 used in FIG. 20A has a narrower X-ray detection range than that of the X-ray detector 21 shown in FIG. 12B.

As described with reference to FIG. 12B, the X-ray generator 13 and the X-ray detector 21 are revolved around the central point C2 serving as the revolution center, and the X-ray CT imaging can be performed for the imaging region R2 similar to that shown in FIG. 12B. However, according to the offset-scanning X-ray CT imaging, the X-ray CT imaging can be performed for the imaging region R1 which is larger than the imaging region R2, by using the X-ray beam BX2.

FIGS. 20B and 20C show specific situations of the offset-scanning X-ray CT imaging. FIG. 20B shows a state of the revolution arm 30 at a time when the offset-scanning X-ray CT imaging is started. FIG. 20C shows a state where the revolution arm 30 is revolved through 180 degrees from the state shown in FIG. 20B. In the offset-scanning X-ray CT imaging, the revolution arm 30 is further revolved from the state shown in FIG. 20C, and returns to an initial position shown in FIG. 20B. During this period, the revolution center of the X-ray generator 13 and the X-ray detector 21 is set at the central point C1.

In the imaging, the X-ray beam BX2 is radiated to only a part of the imaging region R1. However, by revolving the revolution arm 30 through 360 degrees with the revolution center of the X-ray generator 13 and the X-ray detector 21 being set at the central point C1, projection data of an X-ray radiated from each direction equal to or greater than 180 degrees can be obtained with respect to any point within the imaging region R1, thus allowing the offset-scanning X-ray CT imaging for the imaging region R1.

In the present application, the detection surface of the X-ray detector 21 can be made smaller than in the normal X-ray CT imaging by using the method of the offset-scanning X-ray CT imaging. Therefore, the cost of the apparatus can be reduced. That is, by performing the offset-scanning X-ray CT imaging in the X-ray imaging apparatus 100, even though the same detection surface is used, the X-ray CT imaging for a larger imaging region can be performed by an X-ray beam having a small focal spot size which causes a high resolution.

Figure 21A:
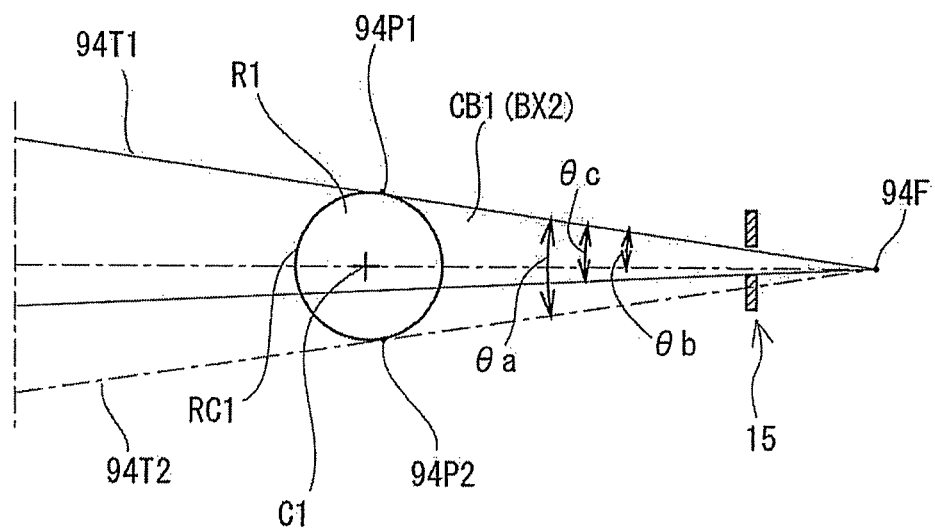
FIGS. 21A and 21B are diagrams for geometrically explaining states of the offset-scanning X-ray CT imaging shown in FIGS. 20B and 20C, respectively.
Figure 21B:
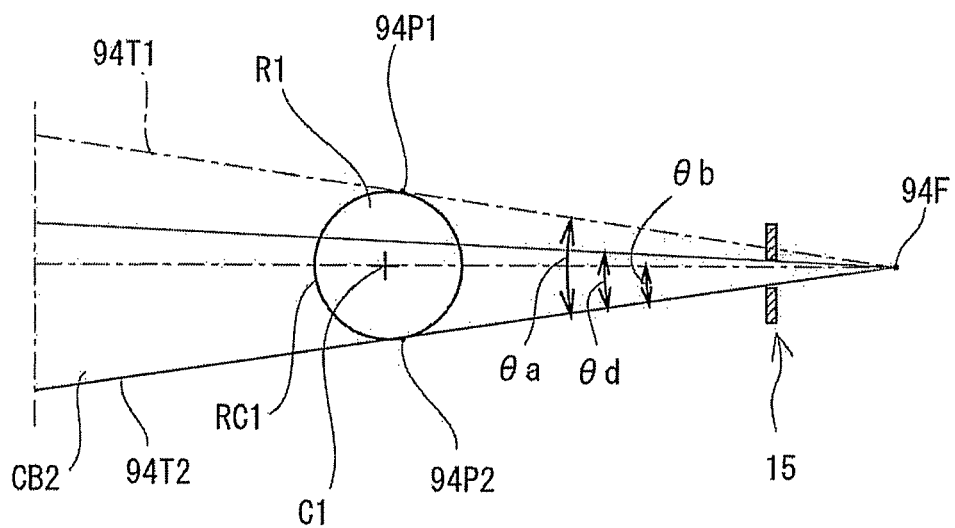

FIGS. 21A and 21B are diagrams for geometrically explaining the states of the offset-scanning X-ray CT imaging shown in FIGS. 20B and 20C, respectively. Features of the offset-scanning X-ray CT imaging will be further described with reference to FIGS. 21A and 21B.

The imaging region R1 has a predetermined largeness in a plane perpendicular to the revolution shaft 31, and has an outline RC1 when seen along the axial direction of the revolution shaft 31. In an example shown in FIG. 21A, the outline RC1 has a circular shape. In FIGS. 21A and 21B, the target surface 94S shown in FIGS. 1A, 1B, and 1C is shown as a focal point 94F. Strictly, the target surface 94S is not a point but a surface. However, in reality, the target surface 94S is a minimal surface, and can be considered as a point when the principle of the offset-scanning X-ray CT imaging is geometrically described.

There are two tangent lines passing through the focal point 94F and being in contact with the outline RC1, to the left and right of the imaging region R1 in a plan view. Here, one of the tangent lines is defined as a tangent line 94T1, and the other is defined as a tangent line 94T2. A tangent point between the outline RC1 and the tangent line 94T1 is denoted by the reference sign 94P1. A tangent point between the outline RC1 and the tangent line 94T2 is denoted by the reference sign 94P2. The angle formed between the tangent lines 94T1 and 94T2 is defined as an angle θa, and the angle (that is, the angle having an angle of θa/2) equally dividing the angle θa is defined as an angle θb.

The offset-scanning X-ray CT imaging uses an X-ray beam CB1 having a spread angle θc (<angle θa) spreading from the tangent line 94T1 toward the tangent line 94T2. The X-ray beam CB1 is continuously radiated to the object M1. Thereby, with respect to any point within the imaging region R1, an X-ray can be radiated from each direction in a range equal to or greater than 180 degrees, and projection data can be obtained.

As shown in FIG. 21B, the offset-scanning X-ray CT imaging may be performed using an X-ray beam CB2 having a spread angle θd (<angle θa) spreading from the tangent line 94T2 toward the tangent line 94T1. An X-ray radiation using the X-ray beam CB1 and an X-ray radiation using the X-ray beam CB2 may be combined with each other to radiate an X-ray from each direction in a continuous range equal to or greater than 180 degrees with respect to each point in the imaging region R1, thereby obtaining projection data. In this case, for example, the revolution arm 30 may be revolved halfway around the object M1 while radiating the X-ray beam CB1, then the X-ray beam CB1 may be switched to the X-ray beam CB2, and the revolution arm 30 may be revolved halfway in the opposite direction. Needless to say, the control of the movement of the revolution arm 30 is not limited thereto.

Preferably, each of the angles θc and θd of the X-ray beams CB1 and CB2 during the offset-scanning X-ray CT imaging is less than the angle θa and equal to or greater than angle θb. Accordingly, if the spread of the X-ray beam changes during the CT imaging, the largeness of the X-ray detection surface of the X-ray detector 21 may be matched to the X-ray beam having the spread angle θa.

More preferably, the spread angles θc and θd of the X-ray beams CB1 and CB2 are kept constant during the CT imaging. In a case where the X-ray radiation using the X-ray beam CB1 and the X-ray radiation using the X-ray beam CB2 are combined with each other, it is preferable that the spread angle θc and the spread angle θd are constant and identical to each other during the CT imaging. This enables the offset-scanning X-ray CT imaging to be appropriately performed by adapting the width of the X-ray detection surface of the X-ray detector 21 to an X-ray beam having a constant spread angle.

In the present application, as described above, CT imaging in which an X-ray beam is continuously radiated to only a part of the imaging region during the CT imaging so that projection data of 180 degrees or more is obtained is defined as the offset-scanning X-ray CT imaging. On the other hand, X-ray CT imaging in which an X-ray beam is continuously radiated to the entire imaging region during the CT imaging is also called normal-scanning X-ray CT imaging.

Among the X-ray CT imaging modes, a mode for performing the offset-scanning X-ray CT imaging is an offset-scanning X-ray CT imaging mode. A mode for performing the normal-scanning X-ray CT imaging is called a normal-scanning X-ray CT imaging mode, in a case where discrimination from the offset-scanning X-ray CT imaging mode is required.

The offset-scanning X-ray CT imaging mode and the normal-scanning X-ray CT imaging mode can be made selectable by the imaging mode selection section 601c, for example. When the offset-scanning X-ray CT imaging mode is selected, the X-ray CT imaging is performed in an imaging orbit as shown in FIGS. 20B and 20C.

7. Seventh Preferred Embodiment

FIGS. 22A to 22E are diagrams for explaining a revolving arm 30B according to a seventh preferred embodiment. FIG. 22A is an overall perspective view of the revolution arm 30B. The revolution arm 30B of this preferred embodiment is configured to rotate an X-ray detection part 20B of the revolution arm 30B around a detection section rotation axis 20C extending in the same direction as the axial direction of the revolution shaft 31. The X-ray detection part 20B includes an X-ray detector 21N having a detection surface for detecting a narrow X-ray beam which is elongated in the same direction as the axial direction of the revolution shaft 31. The X-ray detection part 20B has an X-ray detector 21W mounted on its surface opposite to its surface on which the X-ray detector 21N is mounted. The X-ray detector 21W has a detection surface for detecting an X-ray cone beam. The X-ray detection part 20B is configured to select and use one of these detection surfaces in accordance with an imaging mode.

More specifically, the X-ray detector 21N is used for the panoramic imaging, and the X-ray detector 21W is used for the X-ray CT imaging. In the panoramic imaging, the X-ray detection part 20 is turned to arrange the X-ray detector 21N so as to be opposed to an X-ray generator 13B to detect a narrow X-ray beam. In the X-ray CT imaging, the X-ray detection part 20 is turned to arrange the X-ray detector 21W so as to be opposed to the X-ray generator 13B to detect an X-ray cone beam.

A configuration rotatable relative to the X-ray generation part 10 may be used as the X-ray generator 13B, similarly to the X-ray generator 13A shown in FIGS. 14A and 14B. In an example shown in FIGS. 22A to 22E, the X-ray detector 21W has a detection surface having a width smaller than that of the detection surface of the X-ray detector 21 shown in FIG. 12A, and having such a maximum width so as to allow a detection of an X-ray beam having the same beam width as that of the X-ray beam BX2 shown in FIG. 12B. Needless to say, the X-ray detector 21W may have a detection surface whose size is almost equal to the size of the X-ray detector 21 shown in FIG. 12A.

The rotation of the X-ray detection part 20B around the detection section rotation axis 20C can be performed by driving of a driving source such as a motor (not shown). The X-ray detection part 20B may be automatically rotated in accordance with switching of the imaging mode in the main-body control part 60. Alternatively, the imaging mode in the main-body control part 60 may be switched in association with the rotation of the X-ray detection part 20B. The X-ray detection part 20B may be detached, turned around, and attached again, by hand.

FIG. 22B shows a situation in the panoramic imaging. In a case of the panoramic imaging, an arrangement is made such that the X-ray detector 21N is opposed to the X-ray generator 13 to detect a narrow X-ray beam. An operation of the X-ray imaging apparatus 100 in the panoramic imaging is substantially the same as in FIG. 14B.

FIG. 22C shows a situation in the X-ray CT imaging. In a case of the X-ray CT imaging, an arrangement is made such that the X-ray detector 21W is opposed to the X-ray generator 13 to detect an X-ray cone beam. Specific contents of the X-ray CT imaging are substantially the same as in FIG. 12B.

FIG. 22D shows a situation in the offset-scanning X-ray CT imaging. In a case of the offset-scanning X-ray CT imaging, an arrangement is made such that the X-ray detector 21W is opposed to the X-ray generator 13 to detect an X-ray cone beam. The offset-scanning X-ray CT imaging is the same as that in FIGS. 20B and 20C, or the like.

FIG. 22E shows a situation in the panoramic imaging according to a modification of the seventh preferred embodiment. In this example, the X-ray detector 21N for detecting a narrow beam is eccentrically located so as to detect the X-ray beam BX3 shown in FIG. 12C. Providing the X-ray detector 21N in this manner enables the panoramic imaging to be performed even when the X-ray generator 13B is not configured to rotate relative to the X-ray generation part 10.

The X-ray detection part 20B has the X-ray detectors 21W and 21N corresponding to the respective imaging modes. Therefore, the width of the detection surface of the X-ray detector 21W with respect to a height direction thereof (the width with respect to the same direction as the direction of extension of the revolution shaft 31) may be different from that of the X-ray detector 21N for the panoramic imaging. A width adjusted in accordance with the width of an imaging object (for example, a teeth jaw part) may be adopted.

For example, in an X-ray sensor used for the panoramic imaging, the width of a detection surface with respect to a height direction thereof is often approximately 150 mm. However, in many cases, a width of approximately 120 mm or less is sufficient for the CT imaging of a teeth jaw part. In some cases, a width of approximately 60 mm or less is sufficient for about two to four teeth. In this preferred embodiment, the width of the detection surface of the X-ray detector 21W with respect to the height direction thereof can be adjusted to the minimum necessary one. Accordingly, adoption of the configuration of the X-ray detection part 20B enables a reduction of the cost of the X-ray imaging apparatus 100.

In a case of performing the offset-scanning X-ray CT, even when the width of the X-ray detector 21W with respect to a direction intersecting the revolution shaft 31 is reduced, the X-ray CT imaging of a larger region can be performed as compared with the normal X-ray CT imaging.

8. Modification

Although preferred embodiments of the present invention have been described above, the present invention is not limited to the above-described preferred embodiments, and various modification can be made.

For example, although in the above-described preferred embodiments, the pyramid-shaped X-ray beam is radiated to the imaging region by making the X-ray beam pass through the beam passing hole 151 formed as a rectangular opening in the X-ray CT imaging, a cone-shaped X-ray beam may be radiated by forming the beam passing hole 151 into a circular shape.

In the above-described preferred embodiments, the object holding part 421 fixes a subject, that is, the object M1, in a predetermined position with the object M1 taking a standing posture. However, for example, the object holding part 421 may be configured with a chair or the like which can fix the object M1 with the object M1 taking a sitting posture.

In the above-described preferred embodiments, the revolution shaft 31 is attached to the horizontal movement mechanism including the X- and Y-tables 35, and thereby the revolving arm 30 is moved relative to the object M1 in the horizontal direction. However, for example, it may be also acceptable that the object holding part 421 is configured with a chair or the like, and connected to the horizontal movement mechanism, thereby moving the object M1 relative to the revolving arm 30. It may be also acceptable that a horizontal movement mechanism is provided to each of the revolution shaft 31 and the object holding part 421 so that each of the revolution shaft 31 and the object holding part 421 can be moved in the horizontal direction.

The X-ray CT imaging apparatus 100 of the above-described preferred embodiments is structured so as to vertically stand on a floor. However, needless to say, the X-ray CT imaging apparatus 100 can be applied to a structure in which X-ray CT imaging is performed with the subject, that is, the object M1, taking a lying posture.

Furthermore, the configurations of the respective preferred embodiments and modifications described above may be appropriately combined, unless they are not contradictory with each other.

While the invention has been shown and described in detail, the foregoing description is in all aspects illustrative and not restrictive. It is therefore understood that numerous modifications and variations can be devised by one of ordinary skill in the art without departing from the spirit and the scope of the invention.

What is claimed is:

1. An X-ray imaging apparatus for performing X-ray imaging, comprising:
   an X-ray generation part comprising an X-ray generation source including a cathode and an anode, a surface of the anode opposed to the cathode being formed as an inclined surface inclined with respect to a straight line connecting the anode and the cathode to each other, the inclined surface being formed by an X-ray generation surface which receives an electron beam from the cathode and generates an X-ray, the X-ray generation source generates an X-ray beam which is a flux of the X-ray generated by the X-ray generation surface toward a direction of reflection from the electron beam, the X-ray beam from the X-ray generation part being radiated toward an object;
   an X-ray detection part for detecting the X-ray beam emitted toward the object;
   a revolution drive mechanism for performing X-ray imaging by revolving the X-ray generation part and the X-ray detection part around the object while the X-ray generation part and the X-ray detection part are opposed to each other with the object interposed therebetween;
   an imaging mode selection section for selecting an imaging mode from a plurality of imaging modes having different ranges of radiation of the X-ray beam radiated to the object for X-ray imaging; and
   an emission control section for controlling the X-ray generation part in such a manner that an angle formed between the straight line connecting the cathode and the anode of the X-ray generation source and a central axis of the X-ray beam emitted from the X-ray generation part is increased in an imaging mode having a smaller range of radiation of the X-ray beam.

2. The X-ray imaging apparatus according to claim 1, wherein
   a restriction section restricts the X-ray beam, the restriction section restricting a range of radiation of the X-ray beam by allowing a part of the X-ray beam to pass therethrough in an opening portion thereof, and
   in accordance with a selection signal outputted by the imaging mode selection section, the emission control section controls the restriction section so as to change the range of radiation of the X-ray beam used for the X-ray imaging, by increasing the amount of restriction of an emission range of the X-ray beam at a portion thereof close to the cathode in an imaging mode having a smaller range of radiation of the X-ray beam.

3. The X-ray imaging apparatus according to claim 1, wherein
   the emission control section makes a control so as to displace the X-ray generation source in accordance with a selection signal outputted by the imaging mode selection section, in such a manner that the angle formed between the straight line connecting the cathode and the anode of the X-ray generation source and the central axis of the X-ray beam emitted from the X-ray generation part is increased in an imaging mode having a smaller range of radiation of the X-ray beam.

4. The X-ray imaging apparatus according to claim 3, wherein
   the emission control section controls the displacement of the X-ray generation source by controlling an angle of rotation of the X-ray generation source relative to the X-ray generation part.

5. The X-ray imaging apparatus according to claim 4, wherein
   the X-ray generation source is rotated around a rotation shaft, to be rotated relative to the X-ray generation part.

6. The X-ray imaging apparatus according to claim 5, wherein
   the revolution drive mechanism revolves the X-ray generation part and the X-ray detection part around a revolution shaft, and
   an axial direction of the rotation shaft of the X-ray generation source is set to be a direction parallel to an axial direction of the revolution shaft of the revolution drive mechanism.

7. The X-ray imaging apparatus according to claim 3, wherein
   a restriction section restricts the X-ray beam, the restriction section restricting a range of radiation of the X-ray beam by allowing a part of the X-ray beam to pass therethrough in an opening portion thereof, and
   in accordance with the selection signal outputted by the imaging mode selection section, the emission control section reduces an opening width of the opening portion in the imaging mode having a smaller range of radiation of the X-ray beam.

8. The X-ray imaging apparatus according to claim 1, wherein the plurality of imaging modes include an X-ray CT imaging mode for performing X-ray CT imaging and a panoramic imaging mode for performing panoramic imaging.

9. The X-ray imaging apparatus according to claim 1, wherein
the plurality of imaging modes include a plurality of X-ray CT imaging modes for performing X-ray CT imaging having different sizes of X-ray imaging regions.

10. The X-ray imaging apparatus according to claim 8, wherein
the X-ray CT imaging mode further includes a large-radiation-field X-ray CT imaging mode for performing X-ray CT imaging in a large X-ray imaging region, and a small-radiation-field X-ray CT imaging mode for performing X-ray CT imaging in a small X-ray imaging region.

11. The X-ray imaging apparatus according to claim 8, wherein
the X-ray CT imaging mode includes an offset-scanning X-ray CT imaging mode.

12. The X-ray imaging apparatus according to claim 9, wherein
the X-ray CT imaging mode further includes a large-radiation-field X-ray CT imaging mode for performing X-ray CT imaging in a large X-ray imaging region, and a small-radiation-field X-ray CT imaging mode for performing X-ray CT imaging in a small X-ray imaging region.

13. The X-ray imaging apparatus according to claim 9, wherein
the X-ray CT imaging mode includes an offset-scanning X-ray CT imaging mode.

* * * * *